United States Patent
Laughlin et al.

(10) Patent No.: US 11,809,149 B2
(45) Date of Patent: Nov. 7, 2023

(54) AUTOMATED DEVICE TUNING

(71) Applicant: The Boeing Company, Chicago, IL (US)

(72) Inventors: Brian Dale Laughlin, Wichita, KS (US); Madi L. Laughlin, Wichita, KS (US); Dane B. Laughlin, Wichita, KS (US)

(73) Assignee: The Boeing Company, Chicago, IL (US)

( * ) Notice: Subject to any disclaimer, the term of this patent is extended or adjusted under 35 U.S.C. 154(b) by 169 days.

(21) Appl. No.: 16/827,462

(22) Filed: Mar. 23, 2020

(65) Prior Publication Data

US 2021/0294282 A1    Sep. 23, 2021

(51) Int. Cl.
  *G05B 15/02*    (2006.01)
  *G06N 20/00*    (2019.01)
  *G06F 16/28*    (2019.01)
  *G06F 11/34*    (2006.01)

(52) U.S. Cl.
  CPC .......... *G05B 15/02* (2013.01); *G06F 11/3495* (2013.01); *G06F 16/283* (2019.01); *G06N 20/00* (2019.01)

(58) Field of Classification Search
  None
  See application file for complete search history.

(56) References Cited

U.S. PATENT DOCUMENTS

| | | | | |
|---|---|---|---|---|
| 9,038,959 | B2* | 5/2015 | Andoh | B64G 1/26 244/171.1 |
| 9,492,885 | B2* | 11/2016 | Zediker | E21B 33/13 |
| 2004/0122790 | A1 | 6/2004 | Walker et al. | |
| 2012/0076629 | A1* | 3/2012 | Goff | B64G 1/646 414/730 |

(Continued)

FOREIGN PATENT DOCUMENTS

| | | | |
|---|---|---|---|
| RU | 2676368 | C1 * | 12/2018 |
| WO | 2019207510 | A1 | 10/2019 |
| WO | 2019231282 | A1 | 12/2019 |

OTHER PUBLICATIONS

Arumugam et al., "DAvinCi: A Cloud Computing Framework for Service Robots," IEEE, 2010, 6pg. (Year: 2010).*

(Continued)

*Primary Examiner* — Ryan D. Coyer
(74) *Attorney, Agent, or Firm* — Yee & Associates, P. C.

(57) ABSTRACT

A method, apparatus, and system for controlling a device. A device control system comprises a computer system and a controller in the computer system. The controller receives internal sensor data for a group of internal parameters generated by an internal sensor system that senses the group of internal parameters within the device that relate to an operation of the device and receive external sensor data for a group of external parameters generated by an external sensor system that senses the group of external parameters in an environment around the device that relate to the operation of the device. The controller sends the internal sensor data and the external sensor data for an analysis with (Continued)

aggregated internal sensor data and aggregated external sensor data for devices of a same class as the device to generate results. The controller controls the operation of the device based on the results of the analysis.

47 Claims, 11 Drawing Sheets

(56) References Cited

U.S. PATENT DOCUMENTS

| | | |
|---|---|---|
| 2014/0257047 A1 | 9/2014 | Sillay et al. |
| 2016/0047662 A1* | 2/2016 | Ricci .................. B60N 2/0244 |
| | | 701/540 |
| 2016/0075015 A1* | 3/2016 | Izhikevich .............. B25J 9/163 |
| | | 700/253 |
| 2018/0117769 A1* | 5/2018 | Delazari Binotto ... B25J 11/001 |
| 2018/0299899 A1* | 10/2018 | Suvarna ................ A47L 9/2894 |
| 2019/0110754 A1 | 4/2019 | Rao et al. |
| 2019/0117978 A1 | 4/2019 | Arcot Desai et al. |

OTHER PUBLICATIONS

Doriya et al., "Robotic Services in Cloud Computing Paradigm," IEEE, 2012, 4pg. (Year: 2012).*

Machine Translation for RU 2676368 C1 (Year: 2018).*

Janicki, Benjamin, "Design of a Pneumatic Tool for Manual Drilling Operations in Confined Spaces," University of Washington, 2016, 84pg. (Year: 2016).*

PCT International Search Report, dated Jun. 30, 2021, regarding Application No. PCT/US2021/022525, 16 pages.

\* cited by examiner

AUTOMATED DEVICE TUNING

CROSS-REFERENCE TO RELATED APPLICATION

This application is related to the following patent application: entitled "Automated Deep Brain Stimulation System Tuning", application Ser. No. 16/827,511, filed even date herewith, assigned to the same assignee, and incorporated herein by reference.

BACKGROUND INFORMATION

1. Field

The present disclosure relates generally to an improved data processing system and, in particular, to a method, apparatus, system, and computer program product for automatically tuning a system to cause the system to operate within desired parameters.

2. Background

Devices are used to perform operations in many different situations. For example, a plasma etcher is a device used to remove silicon dioxide from substrates in the production of semiconductor devices. Accuracy of an etch rate of the plasma etcher can depend on etching gases used and processing conditions. When the process conditions change, the etch rate can be adjusted by an amount of activated neutral molecules. This tuning of the etch rate can be tedious and time-consuming for a human operator to make.

In manufacturing of composite materials, a laser cutter is a device that uses a laser beam to vaporize, melt, or otherwise gradually remove material. This device includes optics, an assist gas, and a guidance system to direct and focus the laser beam onto a composite workpiece. The accuracy of the laser cutter can drift over time. Adjustments to the guidance system can be made to ensure a desired amount of accuracy is present.

In another example, a deep brain stimulation system is a device that can operate to treat conditions such as Essential Tremors and Parkinson's Disease through the generation and sending of electrical currents through electrodes implanted in the brain of a patient. These electrical impulses can be directed to specific targets in the brain for the treatment of these and other conditions. Over time, the targets and level of stimulation may need to be adjusted to obtain desired results in the patient. This tuning of the deep brain stimulation system is often made by a doctor or other operator seeing whether changes such as fewer spasmodic musculoskeletal movements or increased motor skills are present. These visual observations are useful but granularity in the level of feedback for making adjustments may be coarser than desired.

As a result, controlling the operation of devices to obtain desired operation of the devices can be more challenging than desired. Therefore, it would be desirable to have a method and apparatus that take into account at least some of the issues discussed above, as well as other possible issues. For example, it would be desirable to have a method and apparatus that overcome a technical problem with making adjustments to a device to obtain desired operation of the device.

SUMMARY

An example of the present disclosure provides a device control system comprising a computer system and a controller in the computer system. The controller is configured to receive internal sensor data for a group of internal parameters generated by an internal sensor system that senses the group of internal parameters within a device that relate to an operation of the device and to receive external sensor data for a group of external parameters generated by an external sensor system that senses the group of external parameters in an environment around the device that relate to the operation of the device. The controller is configured to send the internal sensor data and the external sensor data for an analysis with aggregated internal sensor data and aggregated external sensor data for devices of a same class as the device to generate results. The controller is configured to control the operation of the device based on the results of the analysis.

Another example of the present disclosure provides a device control system comprising a computer system that is configured to receive internal sensor data for a group of internal parameters generated by an internal sensor system that senses the group of internal parameters within a device that relate to an operation of the device. The computer system is configured to receive external sensor data for a group of external parameters generated by an external sensor system that senses the group of external parameters in an environment around the device that relate to the operation of the device. The computer system is configured to analyze the internal sensor data and the external sensor data with aggregated internal sensor data and aggregated external sensor data for devices of a same class as the device to form generate results. The computer system is configured to control the operation of the device based on the results.

Yet another example of the present disclosure provides a method for controlling a device. Internal sensor data is received for a group of internal parameters that relate to an operation of the device. The internal sensor data is generated by an internal sensor system. External sensor data is received for a group of external parameters for an environment around the device. The external sensor data is generated by an external sensor system. The internal sensor data and the external sensor data are analyzed with aggregated internal sensor data and aggregated external sensor data for devices of a same class as the device to generate results. An operation of the device is controlled based on the results.

The features and functions can be achieved independently in various examples of the present disclosure or may be combined in yet other examples in which further details can be seen with reference to the following description and drawings.

BRIEF DESCRIPTION OF THE DRAWINGS

The novel features believed characteristic of the illustrative examples are set forth in the appended claims. The illustrative examples, however, as well as a preferred mode of use, further objectives and features thereof, will best be understood by reference to the following detailed description of an illustrative example of the present disclosure when read in conjunction with the accompanying drawings, wherein:

DETAILED DESCRIPTION

The illustrative examples recognize and take into account one or more different considerations. For example, the illustrative examples recognize and take into account that many factors may need to be considered when tuning a device to operate as desired. The illustrative examples recognize and take into account that this tuning can involve making adjustments to settings for the device to obtain the desired operation of the device. The illustrative examples recognize and take into account that identifying settings to tune a device to operate as desired can be made by taking into account parameters that are both internal and external to the device. The illustrative examples recognize and take into account that difficulty can be present in understanding what data for these parameters indicate about the operation or effectivity of devices. The illustrative examples recognize and take into account that modifications in the operation of the device can be achieved by changing the settings based on the analysis of the data and observing the operation of the device to determine if the changes to the settings provide the desired operation of the device. The illustrative examples recognize and take into account that this type of tuning of settings may not account for things that may be causing a sub-optimization in the operation of the device and which are either unknown to or exacerbated by an operator's choice of setting modifications.

Thus, the illustrative examples provide a method, apparatus, system, and computer program product for controlling a device. In one illustrative example, internal sensor data for a group of internal parameters that relate to the operation of the device is received. The internal sensor data is generated by an internal sensor system. External sensor data for the group of external parameters for an environment around the device is received. The external sensor data is generated by an external sensor system. The internal sensor data and the external sensor data are analyzed with aggregated internal sensor data and aggregated external sensor data for devices of a same class as the device to form an analysis. The operation of the device is controlled based on the analysis.

As used herein, "a group of," when used with reference to items, means one or more items. For example, "a group of internal parameters" is one or more internal parameters.

Figure 1:
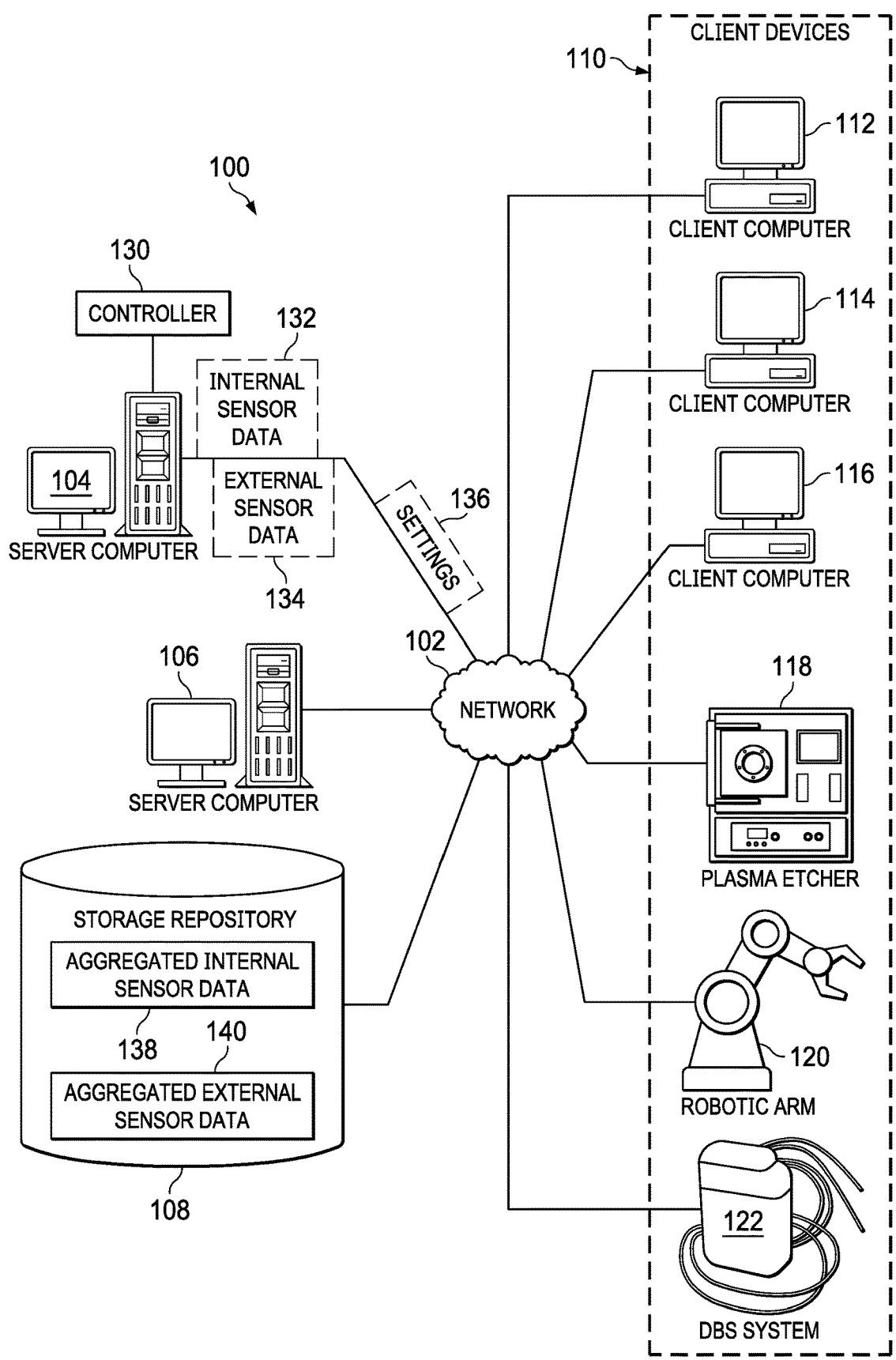
FIG. 1 is a pictorial representation of a network of data processing systems in which illustrative examples may be implemented.

With reference now to the figures and, in particular, with reference to FIG. 1, a pictorial representation of a network of data processing systems is depicted in which illustrative examples may be implemented. Network data processing system 100 is a network of computers in which the illustrative examples may be implemented. Network data processing system 100 contains network 102, which is the medium used to provide communications links between various devices and computers connected together within network data processing system 100. Network 102 may include connections, such as wire, wireless communication links, or fiber optic cables.

In the depicted example, server computer 104 and server computer 106 connect to network 102 along with storage repository 108. In addition, client devices 110 connect to network 102. As depicted, client devices 110 include client computer 112, client computer 114, and client computer 116. Client devices 110 can be, for example, computers, workstations, or network computers. In the depicted example, server computer 104 provides information, such as boot files, operating system images, and applications to client devices 110. Further, client devices 110 can also include other types of client devices such as plasma etcher 118, robotic arm 120, and deep brain stimulation (DBS) system 122. These other types of client devices can include other functionalities in addition to processing information. For example, plasma etcher 118 can receive instructions and settings to etch semiconductor wafers. Robotic arm 120 can process information to perform assembly operations on workpieces such as a wing box or a fuselage for an aircraft. Deep brain stimulation (DBS) system 122 can process information to generate electrical currents to treat symptoms of a human patient.

In this illustrative example, server computer 104, server computer 106, storage repository 108, and client devices 110 are network devices that connect to network 102 in which network 102 is the communications media for these network devices. Some or all of client devices 110 may form an Internet-of-things (IoT) in which these physical devices can connect to network 102 and exchange information with each other over network 102.

Client devices 110 are clients to server computer 104 in this example. Network data processing system 100 may include additional server computers, client computers, and other devices not shown. Client devices 110 connect to network 102 utilizing at least one of wired, optical fiber, or wireless connections.

Program code located in network data processing system 100 can be stored on a computer-recordable storage medium and downloaded to a data processing system or other device for use. For example, settings, program code, and other information can be stored on a computer-recordable storage medium on server computer 104 and downloaded to client devices 110 over network 102 for use on client devices 110.

In the depicted example, network data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers consisting of thousands of commercial, governmental, educational, and other computer systems that route data and messages. Of course, network data processing system 100 also may be implemented using a number of different types of networks. For example, network 102 can be comprised of at least one of the Internet, an intranet, a local area network (LAN), a metropolitan area network (MAN), or a wide area network (WAN).

In this illustrative example, controller 130 is located in server computer 104. As depicted, controller 130 receives sensor data in the form of internal sensor data 132 and external sensor data 134 from client devices 110 selected from at least one of plasma etcher 118, robotic arm 120, deep brain stimulation (DBS) system 122, or other suitable client devices in client devices 110.

As depicted, internal sensor data 132 is for a group of internal parameters generated by an internal sensor system within a device in client devices 110. In this illustrative example, external sensor data 134 is for a group of external parameters in the environment around the device in client devices 110.

In this illustrative example, this data can be received from at least one of plasma etcher 118, robotic arm 120, or deep brain stimulation system (DBS) 122 in client devices 110. This data can be sent over network 102 in data packets using any suitable protocol. In this illustrative example, Transmission Control Protocol/Internet Protocol (TCP/IP) is the protocol used to send data, such as a message containing data, over network 102.

This sensor data can be analyzed by controller 130 to determine settings 136 for using and controlling the operation of at least one of plasma etcher 118, robotic arm 120, or deep brain stimulation system 122 in client devices 110. In determining settings 136, controller 130 can analyze internal sensor data 132 and external sensor data 134 with aggregated internal sensor data 138 and aggregated external sensor data 140 stored in storage repository 108. In this example, aggregated internal sensor data 228 and aggregated external sensor data 230 are aggregations of sensor data from devices of the same class as those in client devices 110.

As depicted, internal sensor data 132 and external sensor data 134 can also be aggregated and stored in storage repository 108. In other words, internal sensor data 132 and external sensor data 134 can be aggregated with aggregated internal sensor data 138 and aggregated external sensor data 140.

Controller 130 can send settings 136 to at least one of plasma etcher 118, robotic arm 120, and deep brain stimulation system (DBS) 122 to control the operation of these devices.

As depicted, controller 130 can control the operation of at least one of plasma etcher 118, robotic arm 120, or deep brain stimulation (DBS) system 122 in client devices 110 to operate with a desired level or means for moving towards operating at a desired level of performance. In the illustrative example, this tuning is performed using the current status of a client device as determined based on internal sensor data 132 and external sensor data 134.

As a client device changes over time or the environment around the client device changes over time, the parameters measured to obtain internal sensor data 132 and external sensor data 134 can change. This change can result in different settings being identified from analyzing sensor data.

The parameters for internal sensor data and external sensor data can take a number of different forms. For example, the parameters for internal sensor data can be selected from at least one a temperature, a light intensity, a frequency, a fluid flow, a pressure, a speed, revolutions, a wavelength, an oxygen level, a fluid viscosity level, an amount of heat at a component, vibrations, a resonant frequency, a magnetic field level, or other suitable parameters. As another example, the parameters for external sensor data can be selected from at least one of a temperature, a light intensity, a fluid flow, a pressure, an altitude, an oxygen level, a precipitation level, a humidity, or other suitable parameters. The particular parameters selected for external sensor data and internal sensor data can be based on the particular device and desired operation of the device.

Thus, the illustrative example takes into account the internal and external conditions by measuring internal parameters and external parameters for client devices 110. This tuning can be performed automatically to adjust client devices 110 to maintain, reach, or move towards desired levels of performance for client devices 110.

Further, the illustrative example uses aggregated sensor data from other client devices in analyzing the sensor data from client devices that are being tuned. In this manner, values for external and internal parameters that may not have been encountered by a client device can be taken into account through the use of aggregated sensor devices from other client devices.

In this illustrative example, a tuning of a client device means that adjustments are made to the device that affects the manner in which the client device operates. The tuning is performed to optimize the performance of the device. This optimization can be performed to maintain, reach, or move towards a desired level of performance for the client device. This adjustment can be made by changing settings, modifying program code, changing configurations, or other suitable changes that change the operation of a client device in a desired manner. In the illustrative examples, the adjustment can be made automatically, manually, or some combination thereof.

The turning performed in the illustrative examples may be based on the standard but does not necessarily need to be based on standard. In the illustrative examples, the tuning in the illustrative examples can address emerging issues or problems with respect to the operation of the devices which may not be understood or even previously known. In the illustrative examples, tuning may be address two issues identified by finding a correlation from all available data, such as aggregated data.

In the illustrative example, the different operations performed to tune client devices 110 take advantage of connectivity to network 102 and the ability to transfer and communicate information to controller 130 using data packets following protocols implemented by network 102. The use of network 102 can enable tuning of client devices 110 in a location where desired connectivity to network 102 is available for client devices 110.

FIG. 1 is intended as an example, and not as an architectural limitation for the different illustrative examples. For example, other client devices can be present in addition to or in place of client devices 110 depicted in FIG. 1. For example, client devices 110 can also include a laser cutter, a computer numeric control lathe, an unmanned aerial vehicle, an unmanned ground vehicle, a five-axis drilling crawler robot, a satellite, or other suitable devices that include processing resources and can communicate over a network. As another example, client device 110 can include 500 or 1,000 deep brain stimulation systems in addition to deep brain stimulation system (DBS) 122.

As used herein, "a number of," when used with reference to items, means one or more items. For example, "a number of different types of networks" is one or more different types of networks.

Further, the phrase "at least one of," when used with a list of items, means different combinations of one or more of the listed items can be used, and only one of each item in the list may be needed. In other words, "at least one of" means any combination of items and number of items may be used from the list, but not all of the items in the list are required. The item can be a particular object, a thing, or a category.

For example, without limitation, "at least one of item A, item B, or item C" may include item A, item A and item B, or item B. This example also may include item A, item B, and item C or item B and item C. Of course, any combinations of these items can be present. In some illustrative examples, "at least one of" can be, for example, without limitation, two of item A; one of item B; and ten of item C; four of item B and seven of item C; or other suitable combinations.

Figure 2:
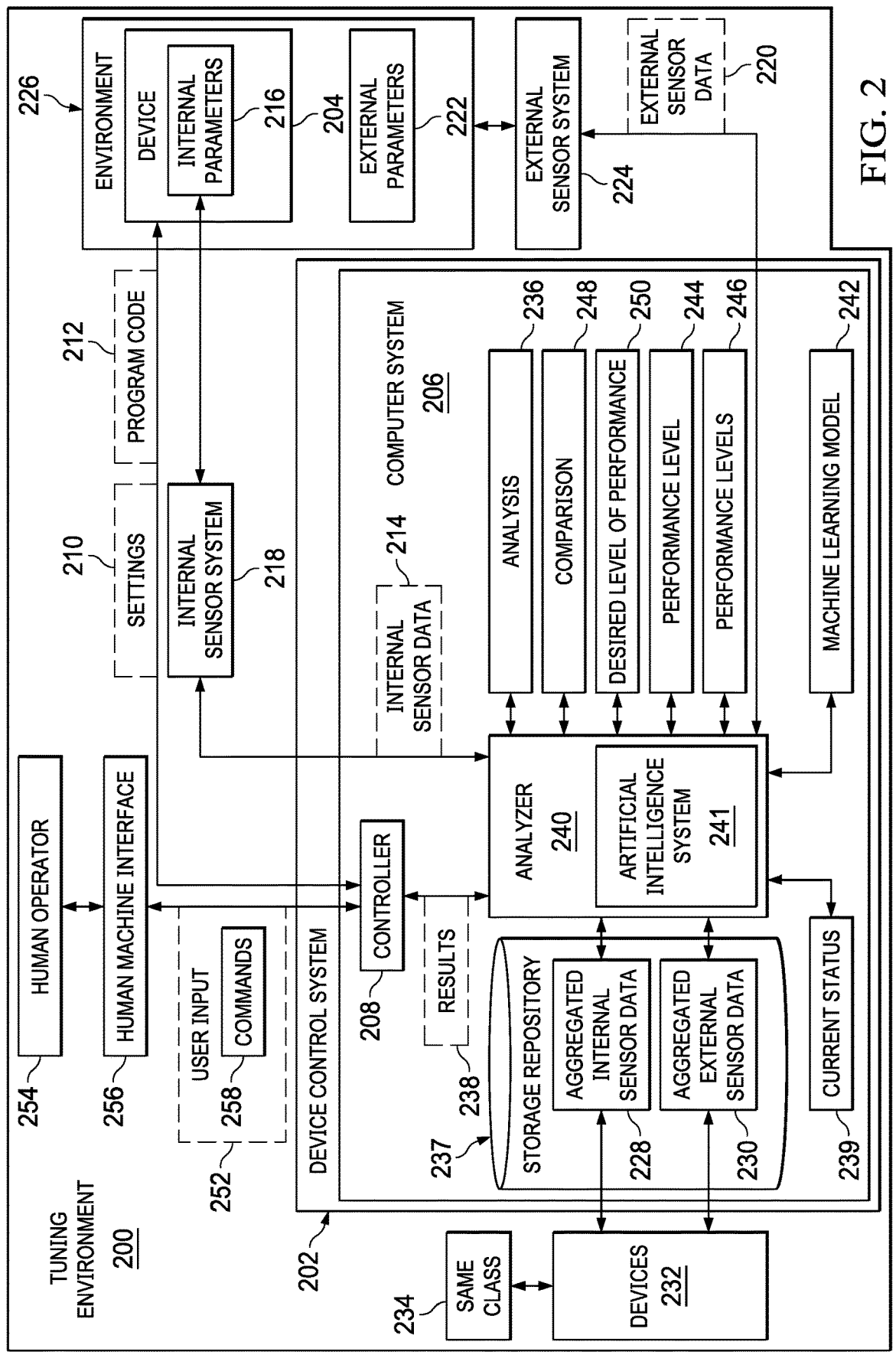
FIG. 2 is an illustration of a block diagram of a tuning environment in accordance with an illustrative example.

With reference now to FIG. 2, an illustration of a block diagram of a tuning environment is depicted in accordance with an illustrative example. In this illustrative example, tuning environment 200 includes components that can be implemented in hardware such as the hardware shown in network data processing system 100 in FIG. 1.

In this illustrative example, device control system 202 in tuning environment 200 can be used to control the operation of device 204. In this illustrative example, device 204 can be any hardware device, object, or system. For example, device 204 can be selected from one of a deep brain stimulation (DBS) system, an infusion pump, a drug pump, a pacemaker, a defibrillator, an exoskeleton, a drone, a manufacturing tool, a maintenance tool, a robotic arm, a robot, a vehicle, an aircraft, a spacecraft, a satellite, a surface control system for an aircraft, or some other suitable device. In the illustrative examples, an infusion pump or a drug pump can be, for example, an insulin pump, an enteral pump, am analgesic pump, a kidney dialysis pump, or other similar types of pumps.

As depicted, device control system 202 comprises computer system 206 and controller 208. Controller 208 is located in computer system 206. Controller 208 can control the operation of device 204. In controlling the operation of device 204, controller 208 is configured to perform a number of different operations.

For example, controller 208 is configured to receive internal sensor data 214 for a group of internal parameters 216 generated by internal sensor system 218 that senses the group of internal parameters 216 within device 204 that relates to the operation of device 204. In this illustrative example, the group of internal parameters 216 can take a number of different forms. For example, internal parameters 216 can be at least one of a temperature, a light intensity, a frequency, a fluid flow, a pressure, a speed, revolutions, a wavelength, an oxygen level, a fluid viscosity level, an amount of heat at a component, vibrations, a resonant frequency, a magnetic field level, or other suitable parameters.

In this illustrative example, internal sensor system 218 senses the group of internal parameters 216 within or on device 204. Internal sensor system 218 comprises one or more sensors. Internal sensor system 218 also may include circuits for preprocessing or, otherwise, processing of sensor data to form internal sensor data 214. The sensors can be located at least one of inside or outside of device 204. In one illustrative example, internal sensor system 218 comprises a group of internal Internet-of-things sensors. In other words, Internet-of-things sensors can generate sensor data from measuring a physical property and can communicate the sensor data over the Internet.

Further, controller 208 is configured to receive external sensor data 220 for a group of external parameters 222 generated by external sensor system 224 that senses the group of external parameters 222 in environment 226 around device 204 that relates to the operation of device 204. In this example, a group of external parameters 222 is for environment 226. In this illustrative example, the group of external parameters 222 can take a number of different forms. For example, external parameters 222 can be at least one of a temperature, a light intensity, a fluid flow, a pressure, an altitude, an oxygen level, a precipitation level, a humidity, or other suitable parameters.

In this illustrative example, external sensor system 224 senses the group of external parameters 222 within or on device 204. External sensor system 224 comprises one or more sensors. In this example, the sensors are located outside of device 204. The sensors are selected and configured to detect external parameters 222 for environment 226 around device 204. External sensor system 224 can also include circuits for preprocessing or, otherwise, processing sensor data to form external sensor data 220. For example, external sensor system 224 can comprise a group of external Internet-of-things sensors.

In the illustrative example, the sensor systems can be in a number of different locations. For example, at least one of internal sensor system 218 or external sensor system 224 can be connected to device 204. When one component is "connected" to another component, the connection is a physical association. For example, a first component, external sensor system 224, can be considered to be physically connected to a second component, device 204, by at least one of being secured to the second component, bonded to the second component, mounted to the second component, welded to the second component, fastened to the second component, or connected to the second component in some other suitable manner. The first component also can be connected to the second component using a third component. The first component can also be considered to be physically connected to the second component by being formed as part of the second component, an extension of the second component, or both.

In other illustrative examples, external sensor system 224 and internal sensor system 218 may not be connected to device 204. In yet other illustrative examples, some sensors in the systems may be connected to device 204 while other sensors in these sensor systems are not connected to device 204.

In this illustrative example, controller 208 is configured to send internal sensor data 214 and external sensor data 220 for analysis 236 with aggregated internal sensor data 228 and aggregated external sensor data 230 for devices 232 of same class 234 as device 204 to generate results 238.

In this example, a device is same class 234 as device 204 when the device has characteristics that are sufficiently close to device 204 such that sensor data from the device can be analyzed with a desired level of accuracy. For example, a newer model of a defibrillator having the same features as a prior model of the defibrillator can be considered to be in the same class as the prior model of the defibrillator.

In the illustrative example, devices 232 of same class 234 are devices having the same characteristics. These characteristics can relate to the functionality of a device. A device having a match in between these characteristics would be of same class 234.

For example, with a device in the form of a pump, characteristics for the pumps of a same class can be selected from at least one of a pressure, cycles, materials forming the pump, a volume of fluid moved, a runtime of the pump, a size, an operating temperature, a type of fluid transported, a displacement mechanism, or other suitable characteristics. One or more of these characteristics may be the characteristics based on the use of the device such as a runtime. The runtime of a device may not be a maximum amount of time but can be the actual period of time that a pump is typically run for a particular use.

In this illustrative example, internal sensor data 214 and external sensor data 220 can be used to determine current status 239 for device 204. In this illustrative example, current status 239 is the status of device 204 at the time that internal sensor data 214 and external sensor data 220 are generated. Current status 239 can be the current state or condition of device 204 based on internal sensor data 214 and external sensor data 220 generated for device 204.

In this illustrative example, aggregated internal sensor data 228 and aggregated external sensor data 230 are stored in a data storage system such as storage repository 237. Storage repository 237 is a hardware system that stores data. Storage repository 237 can also include software for accessing and organizing data. The hardware can take the form of one or more hardware nodes that provide data processing resources to store and access data in storage repository 237. These different nodes can be at the same physical location or distributed in different physical locations. Further, storage repository 237 can be a cloud storage accessed over a connection to a network such as the Internet.

As depicted, controller 208 can send internal sensor data 214 and external sensor data 220 to analyzer 240 for analysis 236. Analyzer 240 is configured to analyze internal sensor data 214 and external sensor data 220 with aggregated internal sensor data 228 and aggregated external sensor data 230 for devices 232 of same class 234 as device 204 to generate results 238 of analysis 236. As depicted, controller 208 can control the operation of device 204 based on results 238 automatically without requiring user input 252 from human operator 254.

In the illustrative example, analyzer 240 can include a number of different components. As depicted in this illustrative example, analyzer 240 comprises artificial intelligence system 241. Artificial intelligence system 241 can include one or more artificial intelligence models such as machine learning models.

In another illustrative example, user input 252 can be received from human operator 254 through human machine interface 256 to control the operation of device 204. For example, human machine interface 256 can be configured to send a set of commands 258 in user input 252 to controller 208. In turn, controller 208 processes the set of commands 258 to control the operation of device 204. The set of commands 258 can, for example, adjust or change settings 210.

As used herein, a "set of," when used with reference to items, means one or more items. For example, a set of commands 258 is one or more of commands 258.

In this illustrative example, analysis 236 can be performed by analyzer 240 using machine learning model 242. Machine learning model 242 can be a part of analyzer 240 or can be accessed by analyzer 240 to perform analysis 236. Analyzer 240 and machine learning model 242 can be located in at least one of device 204, controller 208, a group of data processing systems in computer system 206 in a group of locations remote to device 204, or some other suitable location.

Machine learning model 242 can be trained to perform the analysis of data to generate analysis 236 with results 238 in a number of different ways. For example, machine learning algorithms can be used to train machine learning model 242.

These machine learning algorithms include supervised learning, unsupervised learning, and reinforcement learning. Supervised learning comprises providing the machine with training data and the correct output value of the data. During supervised learning, the values for the output are provided along with the training data (labeled dataset) for the model building process. The algorithm, through trial and error, deciphers the patterns that exist between the input training data and the known output values to create a model that can reproduce the same underlying rules with new data. Examples of supervised learning algorithms include regression analysis, decision trees, k-nearest neighbors, neural networks, and support vector machines.

If unsupervised learning is used, not all of the variables and data patterns are labeled, forcing the machine learning model to discover hidden patterns and create labels on its own through the use of unsupervised learning algorithms. Unsupervised learning has the advantage of discovering patterns in the data without using any labeled datasets. Examples of algorithms used in unsupervised machine learning include k-means clustering, association analysis, and descending clustering.

Supervised learning and unsupervised learning learn from a dataset, while reinforcement learning methods learn from interactions with an environment. Machine learning algorithms such as Q-learning are used to train the predictive model through interacting with the environment using measurable performance criteria.

In this illustrative example, machine learning model 242 can be trained using aggregated internal sensor data 228 and aggregated external sensor data 230 for devices 232 of same class 234 as device 204.

In performing analysis 236 in this particular example, analyzer 240 is configured to compare performance level 244 of device 204 to performance levels 246 for devices 232 of same class 234 using internal sensor data 214 and external sensor data 220 with aggregated internal sensor data 228 and aggregated external sensor data 230 for devices 232 of same class 234 as device 204 to form comparison 248 in analysis 236. Analyzer 240 is also configured to determine whether the status of device 204 is within desired level of performance 250 based on comparison 248. In this illustrative example, comparison 248 can form a part or all of results 238 of analysis 236.

For example, aggregated data, such as aggregated internal sensor data 228 and aggregated external sensor data 230, can be stored in a format that include context. The context can be used to search and retrieved aggregated data. Metadata can be used to associated context with the sensor data for searching and analyzing the sensor data. The context indicates what a piece of data means beyond data itself in isolation. Metadata can be formed using extensible mark language (XML). Extensible mark language can be used to tag sections to later use. The tags can then be used for retrieval of the data.

In this example, desired level of performance 250 can be for device 204. In another illustrative example, desired level of performance 250 can be across all of devices 232 in same class 234 within some statistical variation.

As depicted, controller 208 is configured to control the operation of device 204 based on results 238 of analysis 236. Controller 208 can control the operation of device 204 by changing at least one of settings 210, program code 212, or other features of device 204.

In controlling operation of device 204 by adjusting settings 210 for device 204, controller 208 can send settings 210 to device 204 to control the operation of device 204. As depicted, a setting in settings 210 can be a value for a parameter or variable in device 204 that can be adjusted to control the operation of device 204. Settings 210 can take a number of different forms. For example, settings 210 can include at least one of an amplitude of a current, a voltage, a pulse width, a frequency, a temperature, a speed, an acceleration, a pressure, a direction, an orientation, or other suitable settings, or combinations thereof.

Depending on results 238, controller 208 can control device 204 by sending program code 212 to device 204. Program code 212 can be a patch, an update, or a replacement for current program code run by device 204. Program code 212 can provide at least one of a new feature, a new function, a new algorithm, or modify at least one of an existing feature, an existing function, or any existing algorithm in device 204.

As depicted, in controlling the operation of device 204 based on results 238 of analysis 236, controller 208 can make adjustments to the operation of device 204 using results 238 to obtain desired level of performance 250 for device 204. In illustrative example, these adjustments are not merely a simple comparison in response such as whether the operation is in or out of optimum performance. In the illustrative examples, the adjustments made to the operation of device 204 overcome the limitations of currently employed blind adjustments such as whether the devices in or out of optimal performance.

Thus, in controlling operation of device 204, controller 208 tunes device 204 such that device 204 performs with desired level of performance 250 or at a level that moves towards desired level of performance 250. The process of collecting internal sensor data 214 and external sensor data 220, analyzing sensor data, and controlling operation of device 204 based on the sensor data can be performed repeatedly.

In this manner, the process forms a feedback loop that can be used to automatically control device 204 to perform at desired level of performance 250. This tuning can be performed in response to an event. The event can be at least one of a periodic event or a non-periodic event.

For example, sensor data can be collected and analyzed periodically. For example, data can be collected and analyzed after a period of time, such as a millisecond, five seconds, ten seconds, two minutes, three hours, or some other suitable period of time.

In the illustrative example, a non-periodic event can be, for example, receiving a user input to initiate analysis 236 and controlling of device 204 based on results 238. Another non-periodic event can be when a parameter measured for device 204 exceeds a threshold. For example, if an external parameter such as temperature exceeds a threshold temperature, then the process of collecting and sending sensor data, analyzing sensor data, and controlling the operation of device 204 based on results 238 of analysis 236 can be performed.

In this manner, device control system 202 can continuously tune device 204 to optimize the operation of device 204. This tuning can be performed such that the operation of device 204 at least one of maintains, reaches, or moves toward desired level of performance 250.

At least one of controller 208 or analyzer 240 can be implemented in software, hardware, firmware or a combination thereof. When software is used, the operations performed by at least one of controller 208 or analyzer 240 can be implemented in program code configured to run on hardware, such as a processor unit. When firmware is used, the operations performed by at least one of controller 208 or analyzer 240 can be implemented in program code and data and stored in persistent memory to run on a processor unit. When hardware is employed, the hardware can include circuits that operate to perform the operations in at least one of controller 208 or analyzer 240.

In the illustrative examples, the hardware can take a form selected from at least one of a circuit system, an integrated circuit, an application-specific integrated circuit (ASIC), a programmable logic device, or some other suitable type of hardware configured to perform a number of operations. With a programmable logic device, the device can be configured to perform the number of operations. The device can be reconfigured at a later time or can be permanently configured to perform the number of operations. Programmable logic devices include, for example, a programmable logic array, a programmable array logic, a field programmable logic array, a field programmable gate array, and other suitable hardware devices. Additionally, the processes can be implemented in organic components integrated with inorganic components and can be comprised entirely of organic components excluding a human being. For example, the processes can be implemented as circuits in organic semiconductors.

Computer system 206 is a physical hardware system and includes one or more data processing systems. When more than one data processing system is present in computer system 206, those data processing systems are in communication with each other using a communications medium. The communications medium can be a network. The data processing systems can be selected from at least one of a computer, a server computer, a tablet computer, or some other suitable data processing system.

Figure 3:
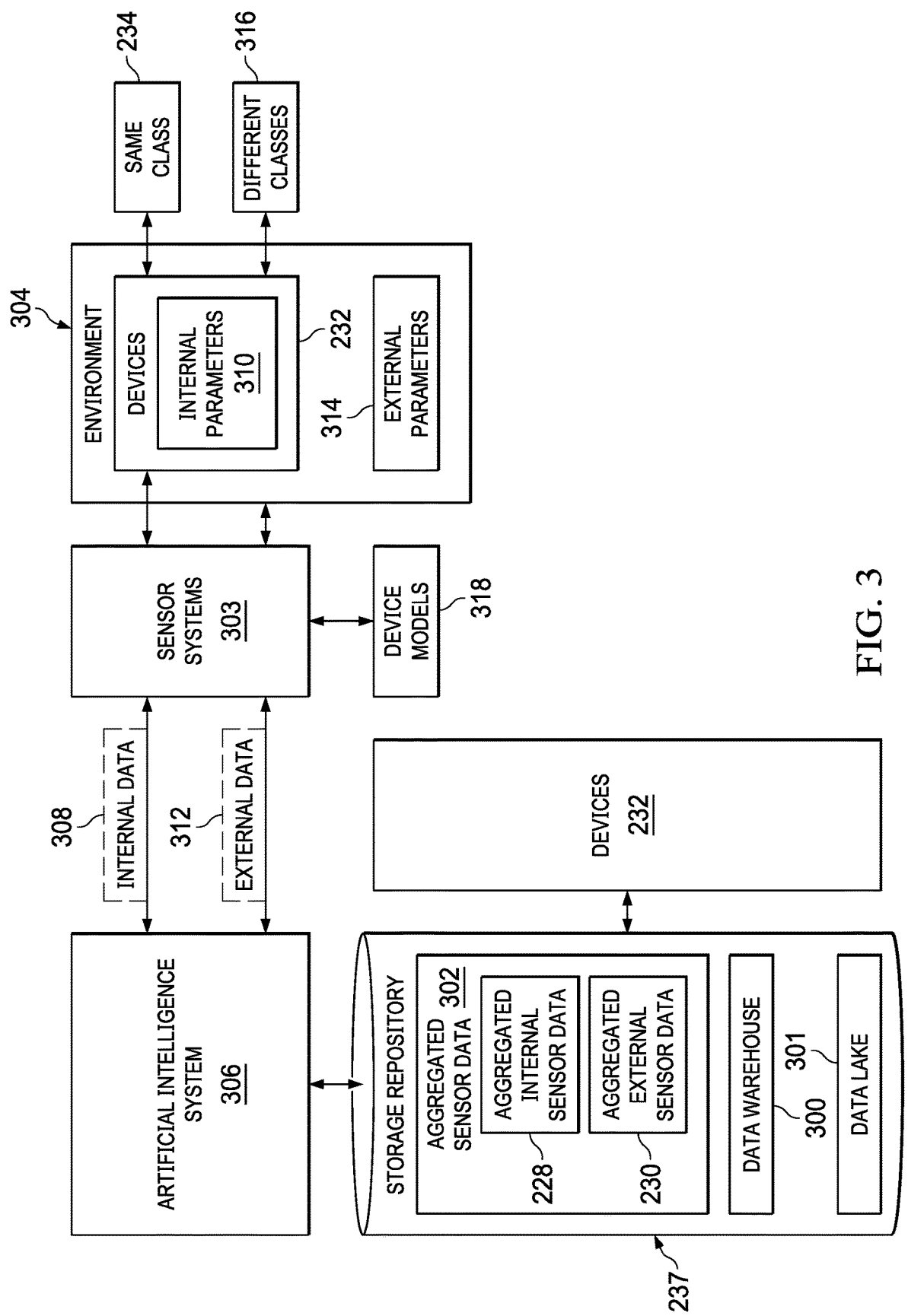
FIG. 3 is an illustration of a block diagram showing aggregation of sensor data in accordance with an illustrative example.

With reference next to FIG. 3, an illustration of a block diagram showing aggregation of sensor data is depicted in accordance with an illustrative example. In the illustrative examples, the same reference numeral may be used in more than one figure. This reuse of a reference numeral in different figures represents the same element in the different figures.

As depicted in this illustrative example, storage repository 237 stores aggregated internal sensor data 228 and aggregated external sensor data 230. As depicted, storage repository 237 can be used to implement storage repository 108 in FIG. 1. In this illustrative example, storage repository 237 includes hardware and can also include software for storing data. For example, storage repository 237 can include more nodes such as computers or processing units which contain storage devices for storing data.

Storage repository 237 can be implemented in a number of different forms. For example, storage repository 237 can be implemented using one or more architectures such as at least one of data lake 300 or data warehouse 301.

As data lake 300, storage repository 237 can store raw data in its native format. Raw data in a native format is data in a form as received from a sensor or other source of the raw data. For example, the data can be sensor data received from a sensor without the formatting or processing for a particular use. The native data can also include, for example, unstructured data such as email messages, documents. The native data can also include binary data such as images, audio, video data, and other similar types of binary data.

This this approach differs from a traditional data warehouse in which data is transformed and processed at the time it is received. In other words, the data in data lake 300 can be stored without first having to structure the data or run any analytics on the data. Further, data lake 300 can also structure data from relational databases, semi-structured data, and binary data.

As data warehouse 301, storage repository 237 can store data in files, folders, or other constructs in a hierarchical fashion. Further, storage repository 237 can be located in a cloud environment in which data is accessed over the Internet.

In this illustrative example, storage repository 237 stores aggregated internal sensor data 228 and aggregated external sensor data 230 as aggregated sensor data 302. Aggregated sensor data 302 is received from multiple sources, such a group of sensor systems 303 monitoring devices 232 and environment 304 around devices 232.

As depicted, storage repository 237 can leverage internal sensor data 132 in FIG. 1 and external data 312 received from sensor systems 303 for many devices, such as devices 232.

This data can include data for situations and environments that may not have been encountered by device 204 in FIG. 2. As a result, the use of aggregated sensor data 302 generated from internal data 308 and external data 312 can be used to more accurately perform analysis 236 and generate results 238 that can be used to control the operation of device 204 such that device 204 operates to at least one of maintain, reach, or move towards desired level of performance 250, as depicted in FIG. 2.

In this illustrative example, storage repository 237 can be used or managed by artificial intelligence system 306. Artificial intelligence system 306 is a system that has intelligent behavior and can be based on the function of a human brain. As depicted, artificial intelligence system 306 comprises at least one of an artificial neural network, a cognitive system, a Bayesian network, a fuzzy logic, an expert system, a natural language system, or some other suitable system. Machine learning is used to train the artificial intelligence system 306. Machine learning involves inputting data to the process and allowing the process to adjust and improve the function of the artificial intelligence system 306. A cognitive system is a computing system that mimics the function of the human brain. The training can be performed on artificial intelligence models such as machine learning models in artificial intelligence system 306.

As depicted, artificial intelligence system 306 is configured to aggregate internal data 308 for a group of internal parameters 310 and external data 312 for the group of external parameters 314 received from a group of sensor systems 303. Artificial intelligence system 306 can be trained to identify features for sensor data of interest for particular situations or environments. Artificial intelligence system 306 can aggregate internal data 308 and external data 312 in a manner that enables a more accurate comparison of aggregated sensor data 302 with internal sensor data 214 and external sensor data 220 received from device 204 in FIG. 2.

In the illustrative example, aggregated data 302 comprises at least one of internal data 308 for internal parameters 310 or external data 312 for external parameters 314 that are combined. In this illustrative example, the data is aggregated over time for a particular device.

In other illustrative examples, the data can be aggregated for groupings of devices 232. For example, devices 232 may be grouped based on factors such as device type, location, environment, or other suitable factors. In one illustrative example, data for devices 232 can be aggregated based on device type.

In one illustrative example, data for parameters such as blood oxygen levels, stress over time, and blood pressure can be combined into a data set for aggregated sensor data 302. This data can also include parameters for the measurement of the performance level of the device.

For example, with an infusion or drug pump such as an insulin pump for example, a blood sugar level and external parameters 314 can be measured and compared with other parameters in aggregated sensor data 302 to determine how the insulin performs in different environments. The different examples can be different people for which the insulin pump is used as well as the environment around the different people. Parameters for sensor data 302 in environment around people can take a number of different forms. For example, these parameters can be at least one of an altitude, a latitude, a longitude, a humidity, a temperature, an ultraviolet radiation level, and oxygen level, a pressure, a wind level, a carbon dioxide level, a carbon monoxide level, or other parameters about the environment around a person. The aggregation of aggregated sensor data 302 can also be grouped based on external parameters 314 describing the people who use the insulin pumps.

Further, different groupings of aggregated sensor data 302 can be created for devices 232 when different classes 316 of devices 232 are present in devices 232. A grouping of aggregated sensor data 302 be created for each class.

In the illustrative example, artificial intelligence system 306 can operate to aggregate data for devices 232. Artificial intelligence system 306 can aggregate data into the same grouping of aggregated sensor data 302 for devices 232 of same class 234.

In yet another illustrative example, the source of internal data 308 and external data 312 can be from devices 232 in the form of device models 318. These device models can be models of actual physical devices such as devices 232. These device models can operate to provide data from many different situations including hypothetical situations that are aggregated by artificial intelligence system 306 as aggregated sensor data 302.

In one illustrative example, one or more technical solutions are present that overcome a technical problem with making adjustments to a device to obtain desired operation of the device. As a result, one or more technical solutions can provide a technical effect of improving the performance of the device. One or more technical solutions can provide a vital technical effect in which the device can be tuned such that the operation of the device maintains a desired level of performance, reaches a desired level of performance, or moves towards a desired level of performance.

Computer system 206 can be configured to perform at least one of the steps, operations, or actions described in the different illustrative examples using software, hardware, firmware, or a combination thereof. As a result, computer system 206 operates as a special purpose computer system in which at least one of controller 208 or analyzer 240 in computer system 206 enables controlling the operation of device 204 in a desired manner that at least one of maintains, reaches, or moves towards desired level of performance 250. In particular, at least one of controller 208 or analyzer 240 can transform computer system 206 into a special purpose computer system as compared to currently available general computer systems that do not have at least one of controller 208 or analyzer 240.

In the illustrative example, the use of at least one of controller 208 or analyzer 240 in computer system 206 integrates processes into a practical application for controlling a group of devices that increases the performance of the group of devices. In other words, at least one of controller 208 or analyzer 240 in computer system 206 is directed to a practical application of processes integrated into at least one of controller 208 or analyzer 240 in computer system 206 that receives internal sensor data for a group of internal parameters that relate to the operation of the device, wherein the internal sensor data is generated by an internal sensor system. At least one of these components in the computer receive external sensor data for the group of external parameters for an environment around the device, wherein the external sensor data is generated by an external sensor system. The computer system with at least one of these components analyzes the internal sensor data and the external sensor data with aggregated internal sensor data and aggregated external sensor data for devices of a same class as the device to generate results and control the operation of the device based on the results.

In this manner, at least one of controller 208 or analyzer 240 in computer system 206 provides a practical application for controlling a device such that the functioning of a group of devices is improved.

Further, these components also improve the operation of computer system 206. For example, at least one of controller 208 or analyzer 240 enable making adjustments or changes to settings for a device such that the device is able to obtain a desired level of performance more quickly or perform more closely to the desired level of performance as compared to using current techniques that do not aggregate internal sensor data and external sensor data from devices in which the aggregated sensor data is used to determine settings for the device.

The illustration of tuning environment 200 in FIG. 2 is not meant to imply physical or architectural limitations to the manner in which an illustrative example may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative example.

For example, one or more devices in addition to device 204 can be controlled by controller 208. A plurality of devices can be present in tuning environment 200, wherein device 204 is part of the plurality of devices. For example, controller 208 can receive the internal sensor data for the group of internal parameters that relate to the operation of a set of devices in addition to device 204, wherein the internal sensor data is generated by the internal sensor systems. The internal sensor system for device 204 also include the sensors in the set of devices. Controller 208 can receive the external sensor data for the group of external parameters for the environment around the set of devices, wherein the external sensor data is generated by a set of external sensor systems. Depending on the implementation and location of device 204. In this example, the external sensor system is all of the sensors that detect the parameters for all of the devices.

Controller 208 can analyze the internal sensor data and the external sensor data with aggregated internal sensor data and aggregated external sensor data for devices of the same class as the set of devices to generate an additional result in addition to the result for device 204. Controller 208 can control the operation of set of devices based the additional result. As result, controller 208 can control device 204 and the set of devices. For example, device 204 can be a deep brain stimulation system and the set of devices can include at least one of a pacemaker, a defibrillator, or a drug pump. In another example, the device 204 can be a robotic arm and the set of devices can include at least one of a tool or an inspection system.

As another example, controller 208 can receive the internal sensor data for the group of internal parameters that relate to the operation from a set of devices in addition to device 204. The set of devices and devices 204 is a plurality of devices. The internal sensor data is generated by the internal sensor systems for the plurality of devices. Controller 208 can also receive the external sensor data for the group of external parameters for the environment around the plurality of devices. The external sensor data is generated by the external sensor systems. Controller 208 can analyze the internal sensor data and the external sensor data with aggregated internal sensor data and aggregated external sensor data for devices of the same class as the plurality of devices to generate the result. Controller 208 can control the operation of the plurality of devices based on the result.

In this example, controller 208 is configured to send the internal sensor data for the plurality of devices and the external sensor data for the plurality of devices for the analysis with the aggregated internal sensor data and the aggregated external sensor data for the devices of the same class as the plurality of devices to form the analysis. Controlling the operation of device 204 based on results 238 of analysis 236 can also include controlling the operation of the plurality of devices based on the results of the analysis for the devices. Each device in the plurality of devices may have a different result. The different result can cause a different adjustment to be made in settings for each device.

As described in the illustrative example, storage repository 237 can be implemented using data lake 300, data warehouse 301, or a combination of these two storage architectures. Further, storage repository 237 can also include other data architectures such as at least one of a data mart, a global file system, or other suitable architectures for storing data. The particular architecture or architectures used can depend on at least one of environment, data type, analysis algorithms, or other factors.

As another example, analyzer 240 can include other components in addition to or in place artificial intelligence system 241. For example, analyzer 240 can also include at least one of an expert system, a knowledge-based system, an intelligent agent system, or a rule-based system.

Figure 4:
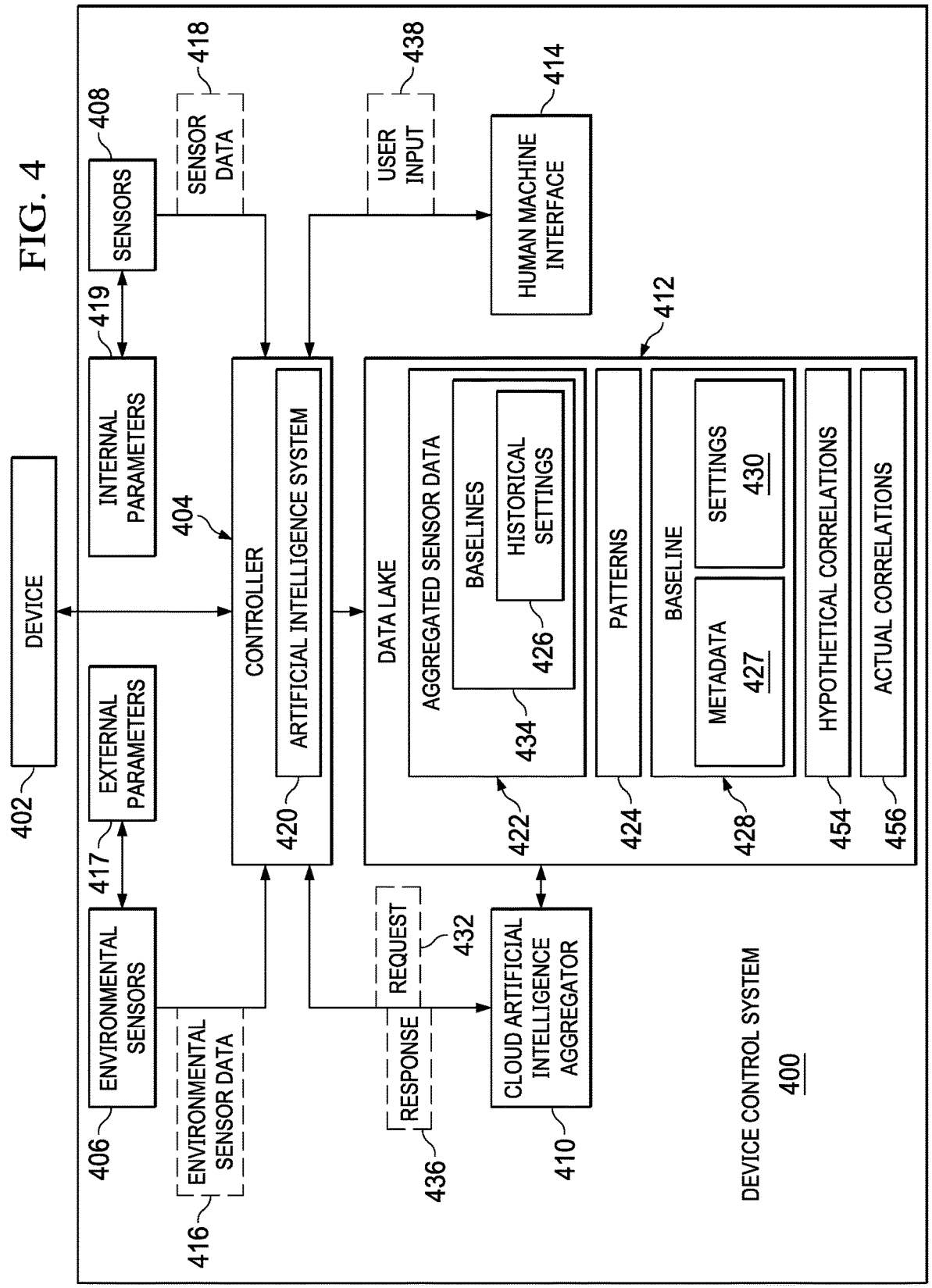
FIG. 4 is an illustration of a block diagram of a device control system for a device in accordance with an illustrative example.

Turning now to FIG. 4, an illustration of a block diagram of a device control system for a device is depicted in accordance with an illustrative example. Device control system 400 is an example of an implementation for device control system 202 in FIG. 2.

As depicted, device control system 400 is configured to control operation of device 402. For example, device control system 400 can control the operation of device 402 to at least one of maintain, reach, or move towards a desired level of performance. This control can be referred to as tuning of device 402. In this illustrative example, device control system 400 can automatically tune the operation of device 402. This automatic tuning is also referred to as an "auto-tune" for device 402.

In this illustrative example, device 402 can take a number of different forms. For example, device 402 can be selected from one of a deep brain stimulation (DBS) system, an infusion or drug pump (e.g., an insulin pump, an enteral pump, an analgesic pump, a kidney dialysis pump, etc.), a pacemaker, a defibrillator, an exoskeleton, a drone, a manufacturing tool, a maintenance tool, a robotic arm, a robot, a vehicle, an aircraft, a spacecraft, a satellite, a surface control system for an aircraft, or some other suitable type of device.

Device control system 400 includes a number of different components. As depicted, device control system 400 comprises controller 404, environmental sensors 406, sensors 408, cloud artificial intelligence aggregator 410, data lake 412, and human machine interface 414.

Environmental sensors 406 are examples of sensors that can be used in external sensor system 224 in FIG. 2. Sensors 408 are examples of sensors that can be used in internal sensor system 218 in FIG. 2. Data lake 412 is an example of an implementation for storage repository 237 in FIG. 2. Cloud artificial intelligence aggregator 410 is an example of an implementation for artificial intelligence system 306 in FIG. 3.

As depicted, controller 404 receives environmental sensor data 416 from environmental sensors 406 and sensor data 418 from sensors 408. The sensors can be Internet-of-things sensors that are connected to a network such as the Internet.

In this illustrative example, environmental sensor data 416 is an example of external sensor data 220 for external parameters 222 in FIG. 2. Environmental sensor data 416 can be data from measurements of external parameters 417 made by environmental sensors 406. External parameters 417 can be selected from at least one of a temperature, a humidity, a pressure, a barometric pressure, a contaminant, an air contaminant, a radioactive contaminant, heat, a noise, a chemical, a location of device 402, an altitude of device 402, or other suitable external parameters for the environment around device 402.

Sensor data 418 is an example of internal sensor data 214 for internal parameters 216 in FIG. 2. Sensor data 418 is data from measurements of internal parameters 419 made by sensors 408 of device 402. For example, internal parameters 419 in sensor data 418 are selected from at least one a temperature, a pressure, a hydraulic pressure, a pressurization time, a force applied, revolutions per minute for a device component, a current level, a speed, an acceleration, a heartbeat rate, an oxygen level, a blood pressure, an electrical current flow, a voltage, an amount of data stored, a battery level, or other suitable data-generated parameters of interest for device 402.

In this illustrative example, sensor data 418 can be received automatically by controller 404 from these sensors. In other examples, sensor data 418 can be received by controller 404 in response to queries or requests made to sensors 408 by controller 404.

Controller 404 can send environmental sensor data 416 and sensor data 418 to cloud artificial intelligence aggregator 410. In this illustrative example, cloud artificial intelligence aggregator 410 operates to manage data lake 412. This management of data lake 412 includes receiving, processing, and storing environmental sensor data 416 and sensor data 418 from different devices as aggregated sensor data 422 in data lake 412. Additionally, cloud artificial intelligence aggregator 410 provides access to aggregated sensor data 422. In another illustrative example, controller 404 can upload environmental sensor data 416 and sensor data 418 directly to data lake 412 for processing by cloud artificial intelligence aggregator 410.

Initially, environmental sensor data 416 and sensor data 418 can be processed by cloud artificial intelligence aggregator 410 to create baseline 428 for device 402. As depicted, baseline 428 can be stored in data lake 412. Additionally, settings 430 for device 402 can be saved in data lake 412. Settings 430 can be associated with or saved as part of baseline 428 for device 402.

In this illustrative example, not all of sensor data 418 and environmental sensor data 416 needs to be saved in data lake 422 as part of baseline 428. For example, parameters can be one or more of internal parameters and external parameters measured for device 402. These parameters can be selected from data that affects the performance of device 402. In other words, these parameters can be selected as parameters that can change and can be analyzed to determine changes to settings 430 to improve or reach a desired level of performance in device 402.

In this illustrative example, the processing of environmental sensor data 416 and sensor data 418 can be performed to determine how different parameters relate to each other. In the illustrative example, this processing can be performed by artificial intelligence system 420 in controller 404. Further, metadata 427 can be included in baseline 428. Metadata 427 can include at least one of a manufacturer, a model, a serial number, a device identifier, a user identifier, or other suitable information.

In this illustrative example, settings 430 can be initially determined for device 402 by comparing baseline 428 to baselines 434. The comparison can be used to identify similar environments for devices of the same class as device 402. Based on identifying similar environments in baselines 434, historical settings 426 for those identified baselines can be used to determine an initial set of settings 430 for device 402.

In this illustrative example, patterns 424 can be used to identify particular environments in baselines 434 and identify historical settings 426 used for those particular environments that provide a desired level performance. Patterns 424 can be patterns in values for a set of parameters for at least one of internal sensor data or external sensor data. The patterns in these parameters can also be used to infer patterns of activity or operation for device 402. The patterns in these parameters can also be used to infer patterns of activity for a person associated with device 402.

In the illustrative example, a pattern in patterns 424 can be determined using one parameter, two parameters, seven parameters, 19 parameters, or some other number of parameters for aggregated sensor data 422 stored in data lake 412. The parameters in a pattern can be from internal sensor data, external sensor data, or some combination thereof.

Those system settings can then be used to adjust settings 430 or form the initial set of settings 430. In other words, artificial intelligence system 420 can determine which ones of patterns 424 are present for a desired level of performance for device 402. Identification of those patterns in patterns 424 can be used to identify historical settings 426 corresponding to those patterns. The identified settings in historical settings 426 can be used to adjust settings 430 in device 402.

For example, with an infusion or drug pump such as an insulin pump for example, patterns for parameters in baselines 434 corresponding to different activity levels of a human user can be used to determine settings 430 for device 402. For example, the parameters for users engaged in scuba diving can be identified. Patterns 424 can be patterns of parameters such as a breathing rate, an oxygen level, a blood pressure, a temperature, and other suitable parameters for a user that corresponds to scuba diving as an activity. Further, the patterns can be identified for the users who have similar characteristics as a user for which the settings are needed. These characteristics can include parameters for weight, age, body fat percentage, or other suitable characteristics.

The identification of these patterns can be used to identify historical settings 426 that result in a desired level of performance such as a desired blood sugar level.

As another example, if a user desires to increase focus for performing a task, settings 430 in device 402 in the form of a deep brain stimulation (DBS) system can be adjusted to increase the focus of the user. In this illustrative example, parameters such as alpha brain waves, cortisol levels, oxygen levels, respiration rate, and other suitable parameters can be measured and compared to at least one of baseline 428 for baselines 434. The use of baseline 428 can be used to determine whether patterns for increased focus are present along with historical settings for the user in baseline 428. Otherwise, patterns 424 can be identified in baselines 434 to identify storable settings that improve the focus of a user. These patterns can also be identified in baselines 434 based on a match or similarity between age, muscle tone, resting heart rate, blood pressure, and other suitable parameters that can be used to identify patterns 424 in baselines 434. Baseline 428 can change with time as additional sensor data is received from device 402. In the illustrative examples, devices can wear, external environments can change, or both can occur. For example, devices over time change due to age and wear. As another illustrative example, an external environment such as a body weight, a season, or a geographic location can change. These types of environmental changes can change various parameters for baseline 428. Further, baseline 428 can also be analyzed to determine trends. These trends can also be analyzed to predict changes to settings 430 for device 402.

In this illustrative example, controller 404 can include artificial intelligence system 420. Artificial intelligence system 420 can be trained and configured to provide functions in controller 404 such as analyzing environmental sensor data 416 and sensor data 418. Further, artificial intelligence system 420 can also provide controller 404 an ability to determine how to control the operation of device 402 as part of tuning device 402 to improve or maintain performance of device 402.

In performing this analysis, artificial intelligence system 420 can use aggregated sensor data 422 in data lake 412 to determine how to tune device 402. As depicted, controller 404 obtains aggregated sensor data 422 from cloud artificial intelligence aggregator 410. As depicted, controller 404 makes request 432 for aggregated sensor data 422. In this example, request 432 can identify a class of devices such that aggregated sensor data 422 of the same class as device 402 is located by cloud artificial intelligence aggregator 410. Further, request 432 can also specify particular values or ranges of values for internal parameters in a device or external parameters in the environment. For example, request 432 can specify that baselines 434 having sensor data matching the values or ranges for particular parameters should be returned.

In response to request 432, cloud artificial intelligence aggregator 410 returns response 436. Response 436 includes aggregated sensor data 422 that is responsive to request 432.

As depicted, controller 404 can analyze aggregated sensor data 422 in response 436 to determine patterns 424 in this data. In this illustrative example, the analysis is made with aggregated sensor data 422 for devices of the same class as device 402.

These patterns can be compared to environmental sensor data 416 and sensor data 418 to determine whether a match is present. Further, historical settings 426 can also be present for aggregated sensor data 422. As a result, when a pattern is found, historical settings 426 in baselines 434 can be examined to determine what settings should be made for device 402.

The results of this analysis can be used to determine changes to device 402 that are intended to increase the performance of device 402. In this manner, device control system 400 provides a feedback loop using at least one of sensor data 418 for device 402 or environmental sensor data 418 for the environment around device 402. With the feedback received, controller 404 can continually tune device 402 to increase or maintain the performance of device 402. The tuning can include at least one of setting changes, program code changes, or other types of changes to device 402.

Further, artificial intelligence system 420 can identify hypothetical correlations 450 in patterns 424. Hypothetical correlations 454 can be used to determine settings 430 for device 402.

For example, a first pattern can have a first set of parameters that have first values that correlate to a second pattern for a second set of parameters that have second values. The correlation can be, for example, the same increase or decrease, a proportional increase or decrease, or some other increase or decrease that is correlated.

In this illustrative example, a correlation in hypothetical correlations 454 is present between the first set of parameters in the first pattern and a second set of parameters in the second pattern when the statistical relationship is present between these two sets of parameters. The presence of a statistical relationship can be determined in a number of different ways. In this example, the presence of a statistical relationship can be determined using a correlation coefficient for the first set of variables in the second set of variables. This correlation coefficient can take a number of different forms selected from at least one of a Pearson product-moment correlation coefficient, an intraclass correlation (ICC), a rank correlation, a polychoric correlation coefficient, or some other suitable type of correlation coefficient.

A threshold can be used to determine when the correlation coefficient is sufficient such that the first pattern and the second pattern are considered to have a hypothetical correlation in hypothetical correlations 454. In other words, hypothetical correlations 454 are correlations that are great enough to be considered statistically significant based on the selection of a threshold.

The threshold can be a preselected value. In another example, the threshold can be determined by artificial intelligence system 420 during training or use of artificial intelligence system 420.

In this illustrative example, correlations are correlations that have been determined to be present based on analysis of patterns 424. Hypothetical correlations 454 are correlations based on hypotheses or determinations that have not been tested to determine whether the correlations are actually present between patterns 424 for which hypothetical correlations 454 have been identified.

In this illustrative example, hypothetical correlations can be used to select settings 430. For example, the first pattern can be a performance parameter that measures a performance level of device 402. The second pattern can be for a temperature for device 402. The correlation between the first pattern and the second pattern may indicate that increasing the temperature was to improve performance level of device 402. In this example, a temperature setting in settings 430 can be set to increase the temperature of device 402 to meet a desired performance level. This temperature setting is tested in device 402 to determine whether an increase the temperature caused by the change in temperature setting results in increased performance of device 402.

The result of settings 430 with a temperature setting that increases the temperature of device 402 can be received in at least one of environmental sensor data 416 for sensor data 418 that includes a parameter is used to measure performance for device 402. The data received from device 402 can determine whether the hypothetical correlation is an actual correlation.

If the hypothetical correlation is the actual correlation, that correlation is stored in actual correlations 456. Actual correlations 456 or correlations between patterns 424 that have been tested and in which at least one of environmental sensor data 416 or sensor data 418 indicates that a correlation is present between the parameters for the two sets of patterns 424. In other words, hypothetical correlations 454 are correlations between patterns 424 identified by artificial intelligence system 420 analyzing aggregated sensor data 422.

Settings 430 can be selected based on one or more hypothetical correlations in hypothetical correlations 454. Settings 430 can be used by device 402. In response to using settings 430 based on the one or more hypothetical correlations in device 402, at least one of environmental sensor data 416 or sensor data 418 is received in this illustrative example. This sensor data can be analyzed by artificial intelligence system 420 to determine whether the one or more of the hypothetical correlations is actually present when used in device 402. When a correlation has been confirmed for a hypothetical correlation in the one or more hypothetical correlations in hypothetical correlations 454, that hypothetical correlation becomes an actual correlation in actual correlations 456. These actual correlations can then be used to select settings for device 402 or other similar devices of the same class as device 402 with greater certainty that the correlations can cause the desired performance of at least one of device 402 and other devices of the same class.

As a result, controller 404 using artificial intelligence system 420 can create new information from aggregated sensor data 422. In other words, artificial intelligence system 420 can perform a transformation of information such as aggregated sensor data 424 into other information such as patterns 422, hypothetical correlations 454, actual correlations 456, or some combination thereof.

For example, artificial intelligence system 420 can identify new information such as at least one of patterns 424, hypothetical correlations 454, or actual correlations 456. For example, artificial intelligence system 420 can identify patterns 424 in aggregated sensor data 422. Patterns 424 can in turn be analyzed by artificial intelligence system 422 to determine hypothetical correlations 454 between patterns 424. These hypothetical correlations can be correlations that have not been previously recognized or identified. The use of hypothetical correlations 454 in settings 430 can be used to determine whether these correlations are actually present in controlling the operation of device 402.

When a hypothetical correlation is determined to be an actual correlation through actual use in device 402, artificial intelligence system 420 adds that correlation to actual correlations 456. Further, the use of settings 430 in device 402 can be performed using simulations without actually needing to implement settings 430 in device 402. In some situations, this type of simulation is more desirable as part of confirming whether a hypothetical correlation is an actual correlation.

This information created by artificial intelligence system 420 from aggregated sensor data 422 is stored in data lake 412 in this depicted example. This information can be used to control the operation of devices such as device 402 based on selecting settings 430 for device 402.

As depicted, device control system 400 also includes human machine interface 414. Human machine interface 414 can be operated by a human operator to generate user input 438. In this example, user input 438 includes commands to programming adjustments, setting changes, or other suitable changes to device 402.

The illustration of device control system 400 is shown for purposes of illustrating one manner in which a device can be controlled, and this illustration is not meant to limit the manner in which other device control systems can be implemented. For example, one or more devices in addition to or in place of device 402 can be controlled by controller 404. In other words, controller 404 can operate to tune the operation of additional devices. These devices can be of the same class or a different class from device 402.

As another example, multiple cloud artificial intelligence aggregators can be present in addition to or in place of cloud artificial intelligence aggregator 410 to manage data lake 412. In other illustrative examples, other data lakes may be present in addition to or in place of data lake 412 for storing aggregated sensor data 422.

Deep brain stimulation is a technique that has been proven to be successful for providing relief and restoring a great degree of motor function for individuals on which this technique is used. This technique has been used to treat disorders and diseases such as Essential Tremors and Parkinson's disease.

With this technique, a deep brain stimulation system comprises a neurostimulator and electrodes that are implanted in the brain of a human patient. The neurostimulator is a controller that sends electrical impulses through implanted electrodes to specific targets in the brain. The electrodes in the deep brain stimulation system can output low-level electrical pulses that effectively buffer and normalize neurological misfiring in the brain.

The illustrative examples recognize and take into account that, currently, a high degree of manual effort is needed to set up the deep brain stimulation system. Further, the illustrative examples recognize and take into account that the deep brain stimulation requires maintenance on a continual basis to ensure that the desired results can be maintained. Further, the illustrative examples also recognize and take into account that problems that patients have can be sporadic in nature and difficult to express when visiting a doctor.

The illustrative examples can employ a device control system to obtain sensor data, analyze the sensor data, and control the operation of the deep brain stimulation system based on the results of the analysis. This process can be formed continually with sensor data being received from measurements of the deep brain stimulation system and the environment around the deep brain stimulation system being used as feedback in a feedback loop.

The illustrative examples employ a device control system as an autotune mechanism for continuous optimization of the operation of the deep brain stimulation system. This process can reduce or avoid the need for manual adjustments or set up by human operators.

The illustrative examples can employ Internet-of-things technology and artificial intelligence systems to continuously monitor and gather sensor data from a deep brain stimulation system and from the environment around the deep brain stimulation system and the patient. The illustrative examples also can leverage use of collecting sensor data in a data lake in analyzing that sensor data with artificial intelligence systems.

Figure 5:
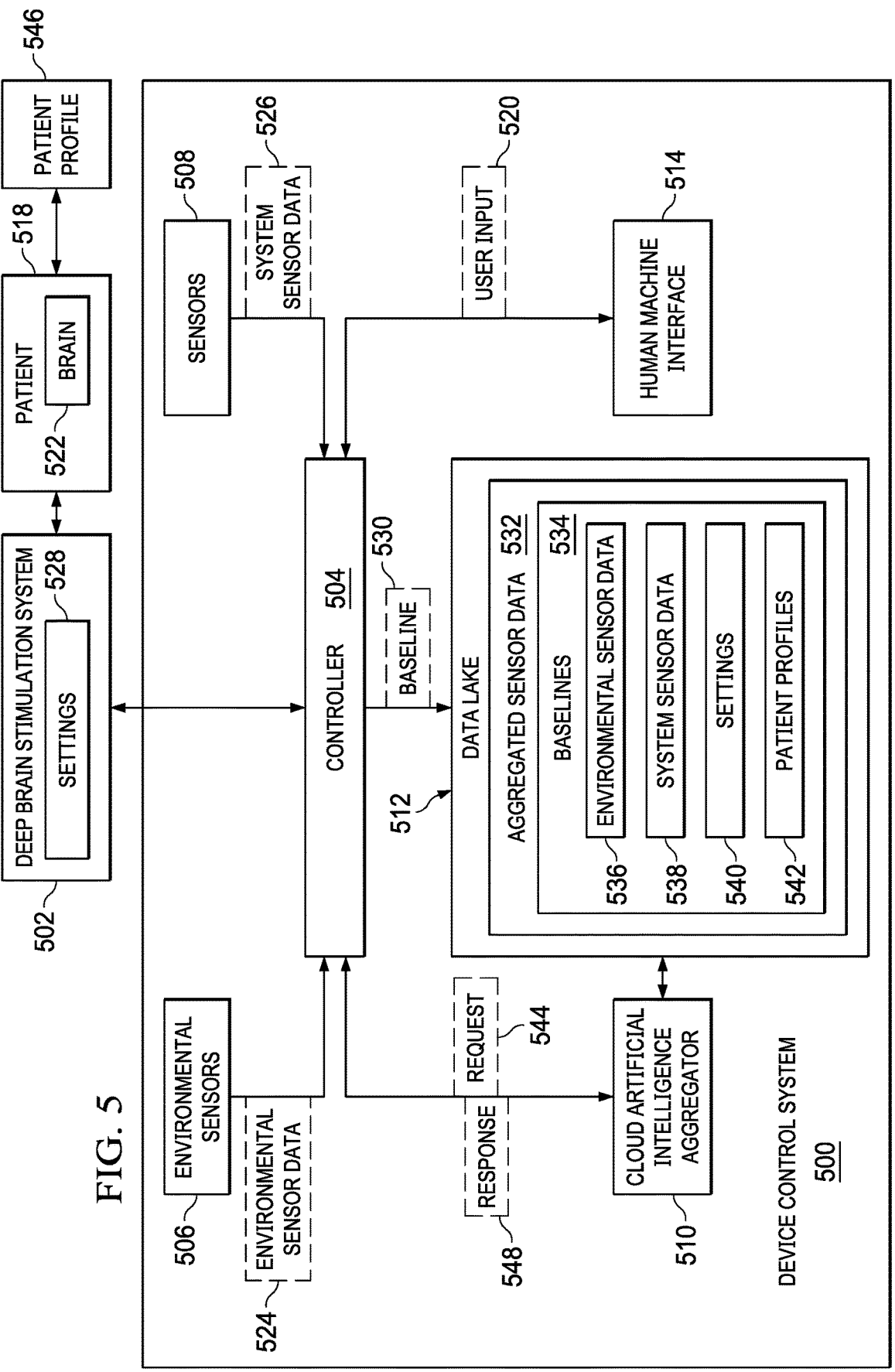
FIG. 5 is an illustration of a block diagram of a device control system for a deep brain stimulation system in accordance with an illustrative example.

Turning to FIG. 5, an illustration of a block diagram of a device control system for a deep brain stimulation system is depicted in accordance with an illustrative example. Device control system 500 is an example of an implementation for device control system 202 in FIG. 2. As depicted, device control system 500 is configured to control the operation of deep brain stimulation system 502. For example, device control system 500 can control the operation of deep brain stimulation system 502 to at least one of maintain, reach, or move towards a desired level of operation. In this illustrative example, device control system 500 can automatically tune the operation of deep brain stimulation system 502.

In this illustrative example, the tuning of deep brain stimulation system 502 is performed to achieve results such as enhanced cognitive abilities, enhanced musculoskeletal coordination control, reduced tremors, increased concentration, or other desired effects.

Device control system 500 includes a number of different components. As depicted, device control system 500 comprises controller 504, environmental sensors 506, sensors 508, cloud artificial intelligence aggregator 510, data lake 512, and human machine interface 514.

In this illustrative example, the flow of information is performed using encryption and other suitable security measures to protect the privacy of patients' personal information. As depicted, health information can be collected from devices for users only when the users have provided consent for the collection and sharing of health information. In this illustrative example, the consent is obtained ahead of time with the proper disclosure and consent forms for privacy rules and regulations, such as the Health Insurance Portability and Accountability Act of 1996. In the illustrative example, health information is not collected or shared unless a user has opted in to share the health information. Further, any other personal information about the patient is not collected or shared without the patient opting in by providing consent to the collection and use of the personal information. For example, audio recordings or video recordings of a patient are not collected or shared without the patient consenting to the collection of sharing of this type of information.

Environmental sensors 506 are examples of sensors that can be used in external sensor system 224 in FIG. 2. Environmental sensors 506 can be Internet-of-things sensors that are connected to a network such as the Internet. The sensors can be, for example, external sensors selected from at least one of an Internet-of-things sensor, a blood pressure sensor, an infusion or drug pump (e.g., an insulin pump, an enteral pump, an analgesic pump, a kidney dialysis pump, etc.), a pacemaker, a defibrillator, a wearable activity tracker, a temperature sensor, a biosensor, a hygrometer, a barometric sensor, a global positioning system unit, a wearable sensor, a bio-sensor, a smartwatch, or other suitable sensors.

In this illustrative example, sensors 508 are examples of sensors that can be used in internal sensor system 218 in FIG. 2. Sensors 508 can be Internet-of-things sensors. Sensors 508 can include at least one of a current sensor, an optical fiber, a voltage detector, a temperature sensor, or other suitable sensors that can take measurements of deep brain stimulation system 502.

In the illustrative example, a biosensor is a device used to the detection of chemical substance. A biosensor can combine a biological sensor element and a transducer element. The biological sensor element can be an element that is at least one of biologically derived material or a biomimetic component. This element is selected as one that at least one interacts with, binds with, or recognizes a substance that is to be detected. The biological sensor element can be for example, at least one of a tissue, a microorganism, an organelle, a cell receptor, an enzyme, an antibody, a nucleic acid, or other suitable components.

In this example, the transducer element is a component that transforms the signal generated by the biological sensor element into a signal that can be used to generated data about the substance that is detected. In this example, the transducer element converts a biochemical signal to an electronic or optical signal.

Data lake 512 is an example of an implementation for storage repository 237 in FIG. 2. Cloud artificial intelligence aggregator 510 is an example of an implementation for artificial intelligence system 306 in FIG. 3.

In this illustrative example, the tuning process can be initiated by a doctor or other health professional using human machine interface 514. Human machine interface 514 includes a display and an input system. Human machine interface 514 can be implemented using at least one of a computer, a tablet computer, a laptop computer, a mobile phone, or some other suitable device. Human machine interface 514 can generate user input 520, which can include a command or instruction to initiate setting up operation of deep brain stimulation system 502 in brain 522 of patient 518.

As depicted, controller 504 receives environmental sensor data 524 from environmental sensors 506 and system sensor data 526 from sensors 508. In this illustrative example, environmental sensor data 516 is an example of external sensor data 220 in FIG. 2. Environmental sensor data 524 can be data from measurements of, for example, at least one of a temperature, a humidity, a pressure, a barometric pressure, a contaminant, an air contaminant, a radioactive contaminant, heat, a noise, a chemical, a location, an altitude, a heart rate, a body temperature, a blood pressure, a blood sugar level, a level of exertion, a respiratory rate, or other suitable external parameters for the environment around deep brain stimulation system 502. In this example, the environment includes at least one of patient 518 and the environment around patient 518.

Controller 504 also receives system sensor data 526 which is an example of internal sensor data 214 in FIG. 2. System sensor data 526 is data generated from measurements of deep brain stimulation system 502. In other words, this sensor data is data based on measurements of at least one of deep brain stimulation system 502 and the environment around deep brain stimulation system 502.

For example, system sensor data 526 can include at least one a temperature, a pressure, a hydraulic pressure, a pressurization time, a force applied, revolutions per minute for device component, a current level, a speed, an acceleration, a heartbeat rate, an oxygen level, a blood pressure, an electrical current flow, a voltage, an amount of data stored, a battery level, or other suitable data-generated parameters of interest for deep brain stimulation system 502.

In this illustrative example, the sensor data can be received automatically by controller 504 from these sensors. In other examples, the sensor data received by controller 504 can be received in response to queries or requests made to the sensors by controller 504.

In this illustrative example, environmental sensor data 524, system sensor data 526, and settings 528 for deep brain stimulation system 502 form baseline 530 for deep brain stimulation system 502 in brain 522 of patient 518. In this illustrative example, settings 528 can include settings for the characteristics of currents emitted by deep brain stimulation system 502. The settings can be selected to direct the current flow to one or more regions in brain 522 of patient 518 with various characteristics.

The settings can include settings for at least one of an electrical current, an amplitude, a voltage, an electrode current flow, a direct current flow, an alternating current flow, a pattern in current flow, a shape of the electrical current flow from electrodes in deep brain stimulation system 502, or a target location of the current flow within a medium when the electrodes in deep brain stimulation system 502 are located in the medium. The pattern of current flow can be the current flow between electrodes in deep brain stimulation system 502, and the current flow can include a pattern of values including pulse length, width, amplitude, and other parameters.

As depicted, controller 504 can send baseline 530 directly to data lake 512. In other illustrative examples, baseline 530 can be sent by controller 504 to cloud artificial intelligence aggregator 510, which saves baseline 530 to data lake 512.

In this illustrative example, data lake 512 provides an ability to store large amounts of datasets for various patients based on a set of defined parameters that are monitored by sensor systems. The amount of data in data lake 512 can enable identifying similar patients based on analyzing aggregated sensor data 532 stored in data lake 512. This identification of matches can be performed using an artificial intelligence system implemented with controller 504.

In the illustrative example, the identification of similar patients is based on identifying groups of data for patients and not actually the actual identity of patients. In other words, the storage and processing data does not specifically track particular patients. Instead, the data is used to track data in groups associate with patients without actually identifying or being able to identify the patients themselves. In other words, in the illustrative example, the data is gathered and stored in a manner that provides the privacy and confidentiality of patients or people from which the sensor data is obtained.

In the illustrative example, health information can be collected from devices for users only when the users have provided consent for the collection and sharing of health information. In this illustrative example, the consent is obtained ahead of time with the proper disclosure and consent forms for privacy rules and regulations, such as the Health Insurance Portability and Accountability Act of 1996. In the illustrative example, health information is not collected or shared unless a user has opted in to share the health information. Further, any other personal information about the user is not collected or shared without the user opting in by providing consent to the collection and use of the personal information. Further, the data is also anonymized to prevent the identification of particular patients in these illustrative examples In this illustrative example, the operation of deep brain stimulation system 502 can be optimized using aggregated sensor data 532 stored in data lake 512. Aggregated sensor data 532 can be baselines 534 for other deep brain stimulation systems used in other patients. As depicted, aggregated sensor data 532 can include environmental sensor data 536, system sensor data 538, settings 540 for different deep brain stimulation systems, and patient profiles 542 for other patients. In this illustrative example, a patient profile in patient profiles 542 contains health information about a particular patient. The patient profile can include information selected from at least one of age, sex, height, weight, blood pressure, family medical history, allergies, illnesses, hospitalizations, medications and dosing, surgeries, vaccinations, chronic diseases, adverse drug reactions, activity level, and other suitable information that is relevant for a patient.

In some illustrative examples, baselines 534 can also include data generated by models of deep brain stimulation systems implanted in human brains. This type of sensor data from models can be used in addition to or in place of actual patient information.

In this illustrative example, controller 504 can send request 544 for baselines 530 for using various criteria. The criteria can specify that baselines 530 should be ones that are for deep brain stimulation systems with the same specifications or class and for patients with similar patient profiles in patient profiles 542 to patient profile 546 for patient 518. In response to request 544, cloud artificial intelligence aggregator 510 sends response 548 with baselines 534 and other information responsive to request 544.

With baselines 534 responsive to request 544, controller 504 can analyze environmental sensor data 524 and system sensor data 526 in baseline 530 using corresponding data in baselines 534. Further, the analysis can also compare patient profile 546 for patient 518 with patient profiles 542 returned in response 548. The analysis can be used to compare baselines of populations in a manner that can be used to determine whether changes to settings 528 for deep brain stimulation system 502 should be made to tune deep brain stimulation system 502 to operate in an optimized fashion. The optimization can be for one or both of optimization of the operation of deep brain stimulation system 502 for the individual patient and the expected operation for the population from which patient profiles 542 are present. With the population, changes in setting can improved the performance for the population as a whole.

The operations are optimized when deep brain stimulation system 502 operates at a desired level of performance, operates to maintain the desired level of performance, or operates in a manner that increases the performance towards the desired level. The optimization to meet a desired level of performance can be for the individual, the expected operation for the population from which patient profiles 542 are present, or both the individual and the population based on improvements from baseline data for the individual and baseline data for the population. Different individuals can have different setting changes to reach the desired level of performance. The desired level of performance can change over time based on changes in at least one of patient profile 546 for patient 518, changes in the environment around patient 518, or changes in deep brain stimulation system 502.

With device control system 500, deep brain stimulation system 502 can be adjusted to provide various improvements in patient 518 or maintain characteristics of patient 518 such as enhanced cognitive ability, enhanced muscular skeletal coordination control, enhanced agility, focused concentration, reduced tremors, or other improvements or characteristics.

As depicted, tuning performed by device control system 500 can be performed continually or as needed based on different non-periodic events using a feedback loop with environmental sensors 506 and system sensors 508 providing sensor data to controller 504, which in turn can send setting changes to deep brain stimulation system 502. Effects of the setting changes can then be detected by environmental sensors 506 and sensors 508 which generate new sensor data which is used as feedback by controller 504 to determine whether additional setting changes should be made.

The tuning with this feedback loop can be made continually or periodically. For example, tuning can be performed once every millisecond, three seconds, seven minutes, two hours, three days, a week, or at some other period of time. This periodic tuning can be in addition to or in place of tuning based on events that are non-periodic.

In this illustrative example, tuning can also be performed when some parameters measured by environmental sensors change beyond a selected threshold. For example, the tuning can be performed if a particular pollutant, pesticide, solid, or other toxin detected by environmental sensors 506 exceeds a threshold level.

Another event that can result in initiating tuning of deep brain stimulation system 502 by device control system 500 is a change in activity level that exceeds a threshold. The activity level can be, for example, an amount of daily or weekly exercise. This exercise can be determined based on environmental sensor data such as a heartrate, an oxygen level, a respiration rate, a temperature, and other sensor data that can be used to determine the activity level of patient 518.

Another non-periodic event that can result in initiating tuning of deep brain stimulation system 502 is an improvement in settings 540 for deep brain stimulation systems for patient profiles 542 that correspond or sufficiently match patient profile 546 for patient 518. A change in the settings for a population similar to patient 518 can be used to initiate analysis and changes in settings 528 for deep brain stimulation system 502 to control the operation of this device as part of a tuning process.

Thus, device control system 500 enables identifying patient profiles 542 that are the same or sufficiently close to patient profile 546 to be considered a match. For example, patient profile 546 can be considered sufficiently close to another patient profile in patient profiles 542 if the value of a parameter in both patient profiles fall within the same range of values designated for the parameter. For example, with deep brain stimulation system 502, parameters can be compared to find patient profiles 542 that are exact matches or sufficiently close that affect neurological functions. The range of values for these parameters can be based on current standards in which the neurological function is expected to the same for that range of values for a particular parameter.

For example, with a parameter form of a blood oxygen level, altitude levels can change the blood oxygen level. A change in the blood oxygen level can change oxygen supply to the brain, which can affect neurological functions. As a result, ranges of blood oxygen levels can be selected in which each range of the blood oxygen level can be expected to have the same level of neurological function.

As another example, age can be divided into ranges and used to determine when patient profile 546 is set efficiently close to one or more of patient profiles 542. Two patient profiles can be sufficiently close to each other when the age for those profiles are within the same age range. The age range can be selected based on when changes occur in neurological functions in the brain.

As another illustrative example, a body mass index (BMI) is a parameter that can have a range in which the neurological function is expected to be the same within the range selected for the body mass index. Other parameters for which ranges can be used for identifying similar patient profiles include, for example, without limitation, geographic region, ancestry, and other parameters describing patients and patient profiles 542.

Further, patient profiles can be considered to be sufficiently close when a selected number of parameters all have values falling within the same ranges for those parameters. The selection parameters for this type of matching can be based on which parameters affect levels of neurological functions.

This identification of similar patient profiles can be performed with the ability to store very large amounts of data in data lake 512 and analyze the data using an artificial intelligence system implemented in controller 504 to perform the analysis. As a result, similar patients that can be identified may not be easy to locate using current techniques and available data. With the identification of patient profiles and settings for the patient profiles, adjustments can be made to the operation of deep brain stimulation system 502 that are more effective as compared to adjustments made using current techniques in which the analysis is performed by a human operator such as a doctor, a researcher, or a technician.

The illustration of device control system 500 used for tuning the operation of deep brain stimulation system 502 in FIG. 5 is provided for purposes of illustrating one manner in which device control system 500 can control devices. This illustration is not meant to limit the manner in which other illustrative examples can be implemented. For example, device control system 500 can be used to control the operation of other devices that may be used by the same patient. For example, device control system 500 can be used to tune the operation of other medical devices such as at least one of an infusion or drug pump (e.g., an insulin pump, an enteral pump, an analgesic pump, a kidney dialysis pump, etc.), a pacemaker, a defibrillator, a drug delivery unit, or some other medical device.

In another example, device control system 500 can operate to control the operation of one or more deep brain stimulation systems in addition to or in place of deep brain stimulation system 502.

Further, the illustrative example enables individual programming for a particular patient that can be continuously optimized to provide a desired level of stimulation for electrical current by deep brain stimulation system 502 for a patient that can take into account various variables such as patient health, an exertion level, a stress level, a blood sugar level, a heart rate, a blood oxygen level, a body temperature, a serum level for a hormone, a respiratory rate, a respiratory volume, a blood pressure, or other suitable parameters relating to the patient that may be relevant for controlling operation of deep brain stimulation system 502.

Figure 6:
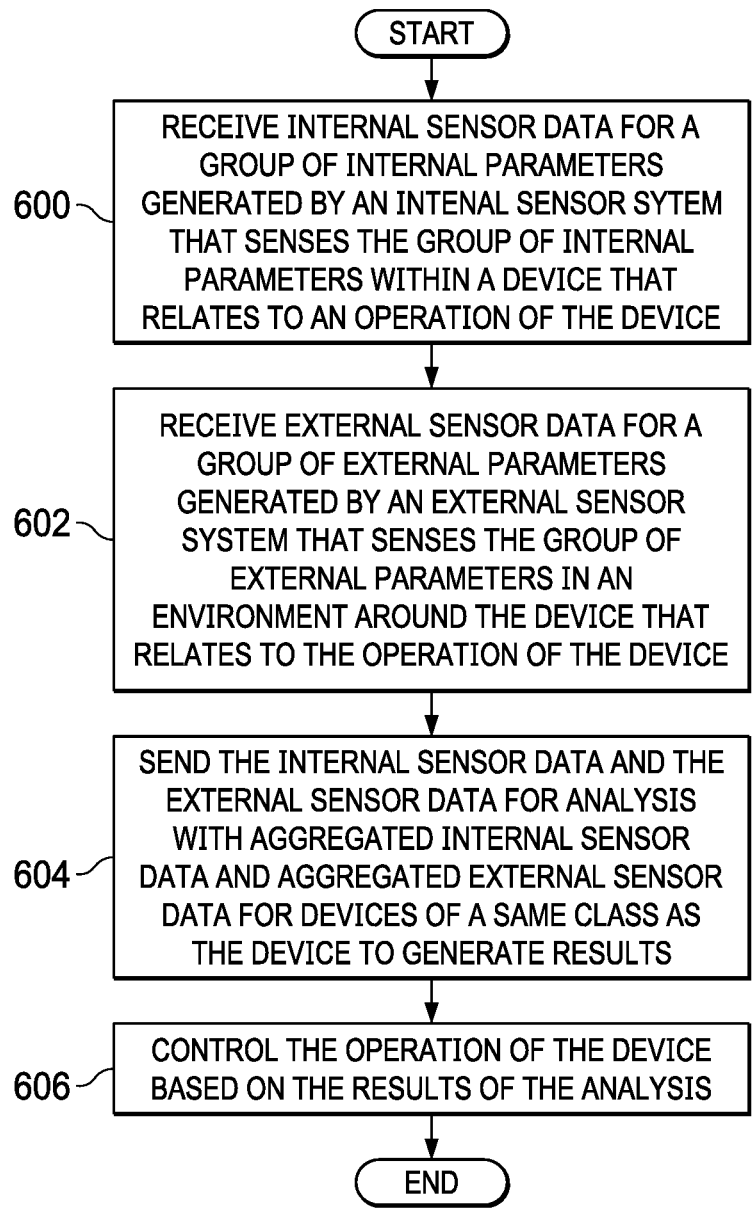
FIG. 6 is an illustration of a flowchart of a process for controlling a device in accordance with an illustrative example.

With reference to FIG. 6, an illustration of a flowchart of a process for controlling a device is depicted in accordance with an illustrative example. The process in FIG. 6 can be implemented in hardware, software, or both. When implemented in software, the process can take the form of program code that is run by one or more processor units located in one or more hardware devices in one or more computer systems. For example, the process can be implemented in controller 208 in computer system 206 in FIG. 2.

The process begins by receiving internal sensor data for a group of internal parameters generated by an internal sensor system that senses the group of internal parameters within a device that relates to an operation of the device (operation 600). The process receives external sensor data for a group of external parameters generated by an external sensor system that senses the group of external parameters in an environment around the device that relates to the operation of the device (operation 602).

The process sends the internal sensor data and the external sensor data for analysis with aggregated internal sensor data and aggregated external sensor data for devices of a same class as the device to generate results (operation 604).

The process controls the operation of the device based on the results of the analysis (operation 606). The process terminates thereafter. In operation 606, the process can send settings to the device based on the results. For example, the results may include settings suggested for the device. The settings can change the operation or configuration of the device to reach a desired level of performance. In other illustrative examples, the process can update or send program code to the device.

This process can be repeated any number of times dynamically during operation of the device to operate as a control loop. In this manner, the device can be tuned based on an event that is periodic or non-periodic. The periodic event can be performing the process every five seconds, one minute, ten minutes, two hours, or some other time period. As another example, the process can be initiated by the controller when a parameter of being monitored exceeds a threshold.

Figure 7:
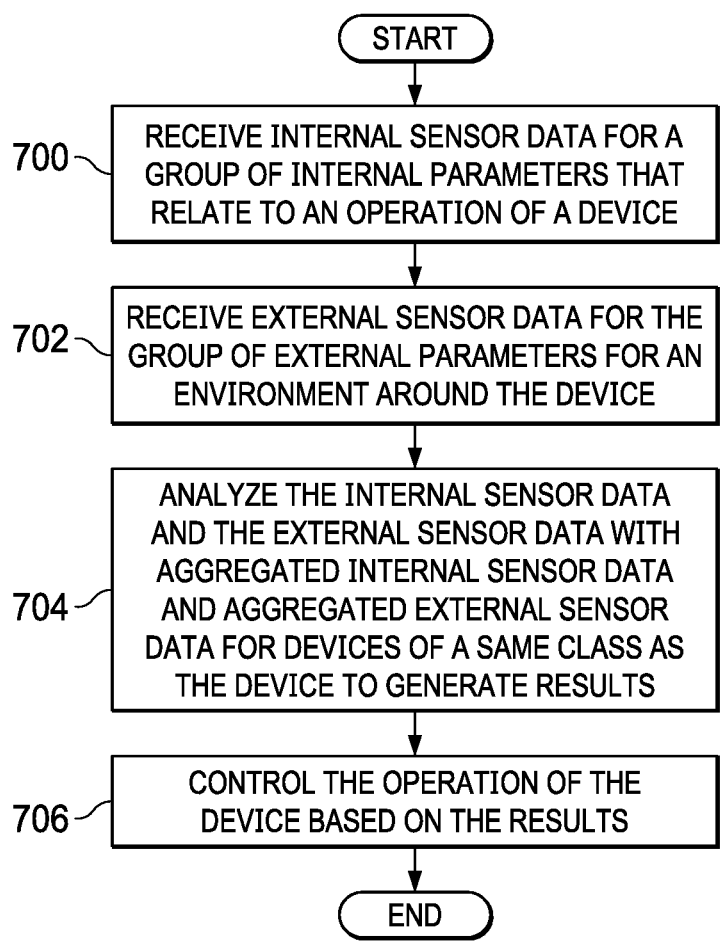
FIG. 7 is an illustration of a flowchart of a process for controlling a device in accordance with an illustrative example.

Turning next to FIG. 7, an illustration of a flowchart of a process for controlling a device is depicted in accordance with an illustrative example. The process in FIG. 7 can be implemented in hardware, software, or both. When implemented in software, the process can take the form of program code that is run by one or more processor units located in one or more hardware devices in one or more computer systems. For example, the process can be implemented in analyzer 240 in computer system 206 in FIG. 2.

The process begins by receiving internal sensor data for a group of internal parameters that relate to an operation of a device (operation 700). The internal sensor data received in operation 700 is generated by an internal sensor system.

The process receives external sensor data for a group of external parameters for an environment around the device (operation 702). In this operation, the external sensor data is generated by an external sensor system.

The process analyzes the internal sensor data and the external sensor data with aggregated internal sensor data and aggregated external sensor data for devices of a same class as the device to generate results (operation 704). The process controls the operation of the device based on the results (operation 706). The process terminates thereafter. In operation 706, the results can include suggested settings, commands, configurations, or other information that can be used by a controller to tune the operation of the device to reach a desired level of performance.

Figure 8:
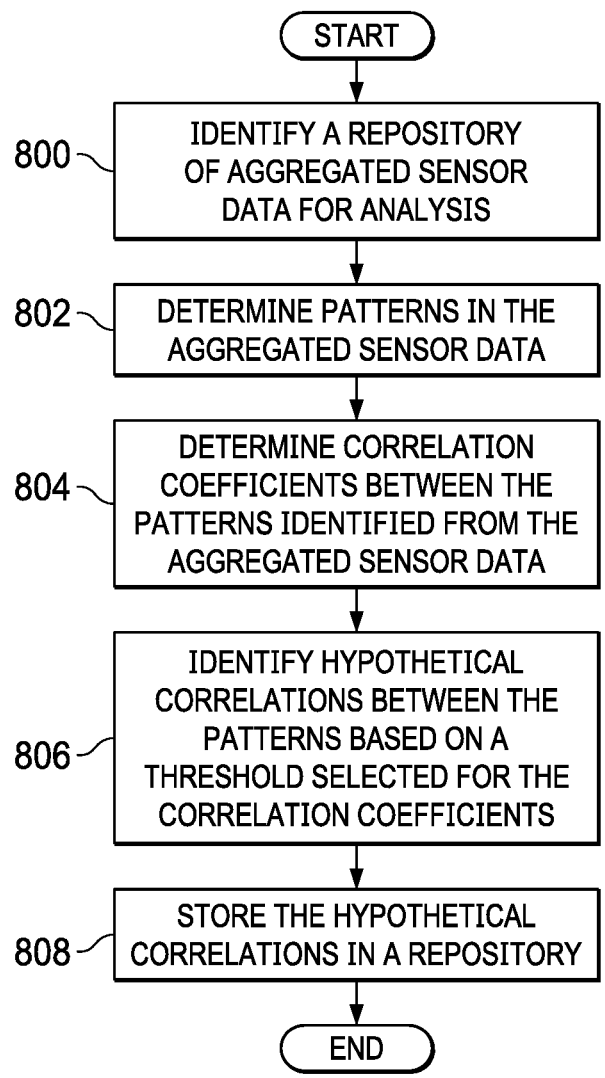
FIG. 8 is an illustration of a flowchart of a process for identifying hypothetical correlations in patterns in aggregated sensor data in accordance with an illustrative example.

With reference to FIG. 8, an illustration of a flowchart of a process for identifying hypothetical correlations in patterns in aggregated sensor data is depicted in accordance with an illustrative example. The process in FIG. 8 can be implemented in hardware, software, or both. When implemented in software, the process can take the form of program code that is run by one or more processor units located in one or more hardware devices in one or more computer systems. For example, the process can be implemented in controller 208 in computer system 206 in FIG. 2 and in analyzer 240 in FIG. 4. As a more specific illustrative example, these processes can be implemented in artificial intelligence system 241 in FIG. 2 and artificial intelligence system 420 in FIG. 4.

The process begins by identifying a repository of aggregated sensor data for analysis (operation 800). The repository can be, for example, a data lake such as data lake 412 in FIG. 4 or data lake 512 in FIG. 5. In other examples, the repository can take other forms or combinations of forms in addition to or in place of the data lake including at least one of a data mart, a data warehouse, a global file system, or some other suitable architecture for storing data.

The process determines patterns in the aggregated sensor data (operation 802). A pattern can be for data for one or more parameters. These parameters can be at least one of an internal parameter for a device or an external parameter for the environment around the device. When the device is a deep brain stimulation system or some other implantable device that can be implanted in a human being, the environment can be for parameters in the body. Further, the environment can also can be for parameters measured in the environment around the body. In other words, the parameters can include both the human being and the environment around the human being.

Additionally, one pattern may be a pattern of data for one parameter while another parameter can be a pattern of data for three parameters, seven parameters, or some other number of parameters. In other words, different patterns may be patterns of data for different numbers of parameters.

The process determines correlation coefficients between the patterns identified from the aggregated sensor data (operation 804). For example, a hypothetical correlation can be present between the parameters in a first pattern and a parameter in a second pattern when a statistical relationship is present between these two parameters. In this illustrative example, the statistical relationship can be determined using a correlation coefficient calculated between the first parameter and a second parameter. This correlation coefficient can take a number of different forms selected from at least one of a Pearson product-moment correlation coefficient, an intraclass correlation (ICC), a rank correlation, a polychoric correlation coefficient, or some other suitable type of correlation coefficient.

The process then identifies hypothetical correlations between the patterns based on a threshold selected for the correlation coefficients (operation 806). In operation 806, a threshold be selected to indicate when the correlation coefficient is sufficient such that the first pattern and the second pattern considered have a hypothetical correlation with each other.

The process stores the hypothetical correlations in a repository (operation 808). The process terminates thereafter. The repository in operation 808 can be the same repository that stores the aggregated sensor data.

Figure 9:
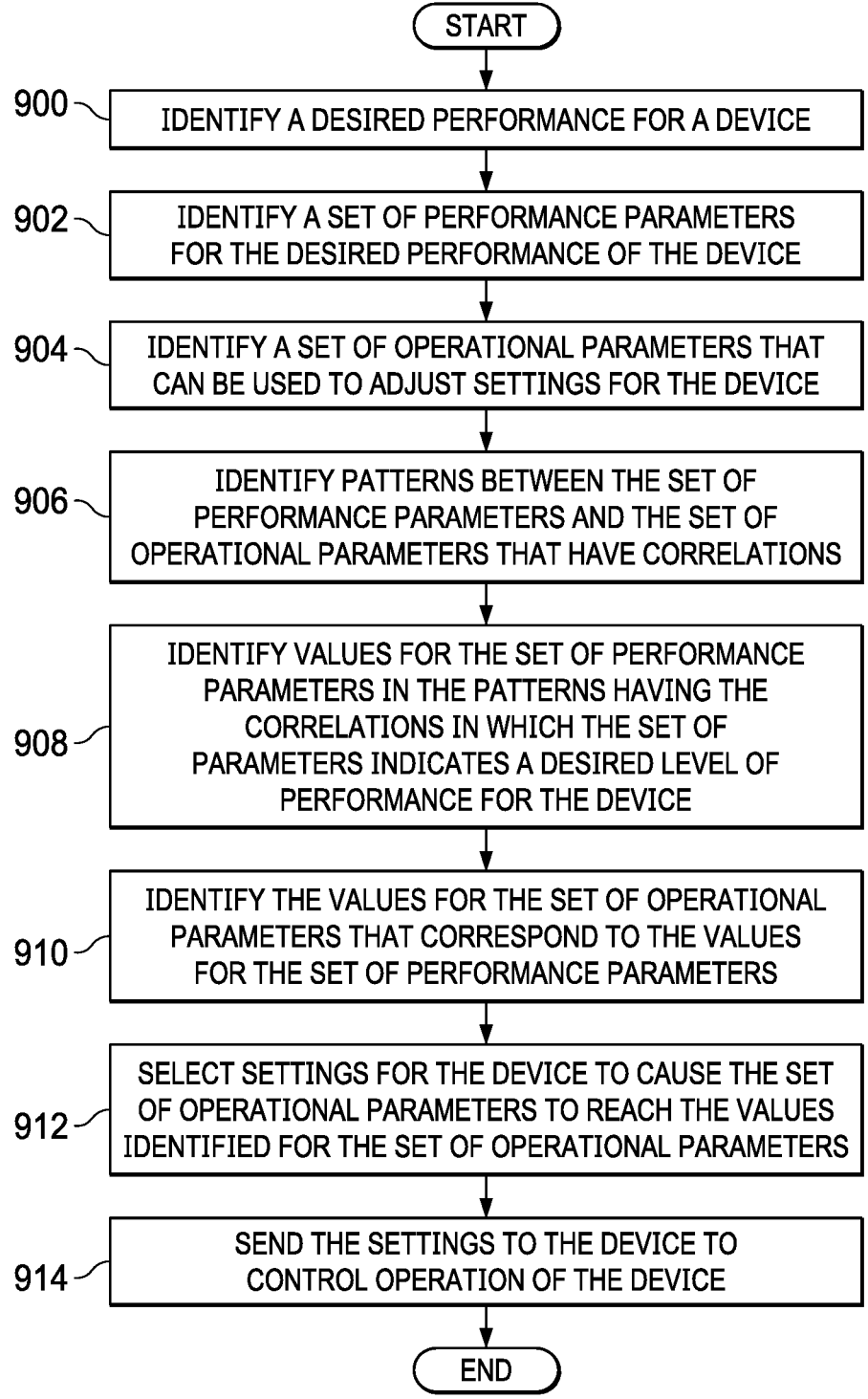
FIG. 9 is an illustration of a flowchart of a process for selecting settings for a device from correlations in accordance with an illustrative example.

Turning to FIG. 9, an illustration of a flowchart of a process for selecting settings for a device from correlations is depicted in accordance with an illustrative example. The process in FIG. 9 can be implemented in hardware, software, or both. When implemented in software, the process can take the form of program code that is run by one or more processor units located in one or more hardware devices in one or more computer systems. For example, the process can be implemented in controller 208 in computer system 206 in FIG. 2 and in analyzer 240 in FIG. 4. As a more specific illustrative example, these processes can be implemented in artificial intelligence system 241 in FIG. 2 and artificial intelligence system 420 in FIG. 4.

The process begins by identifying a desired performance for a device (step 900). This desired performance can be, for example, to operate a tool to perform manufacturing operations at a selected rate, to operate a deep brain stimulation system to reduce tremors to a desired amount, to operate a drug pump, to obtain a desired effect such as pain reduction or reducing a glucose level, or some other type of desired performance.

The process identifies a set of performance parameters for the desired performance of the device (operation 902). The set of performance parameters is one or more parameters that measure the performance of the device. For example, a performance parameter can be a hole drilling rate for a tool performing a manufacturing operation. Performance parameters can be a glucose level for a drug pump that pumps insulin.

The process identifies a set of operational parameters that can be used to adjust settings for the device (step 904). The set of operational parameters are parameters that can be measured from the device and can be used to select settings for the device. For example, the set of operational parameters can be a drug delivery rate for a drug such as insulin. As another example, the set of operational parameters can be a drug delivery rate for a pain reliever.

The process identifies patterns between the set of performance parameters and the set of operational parameters that have correlations (operation 906). In operation 906, these correlations can be hypothetical correlations or actual correlations.

The process then identifies values for the set of performance parameters in the patterns having the correlations in which the set of parameters indicate a desired level of performance for the device (operation 908). The process then identifies the values for the set of operational parameters that correspond to the values for the set of performance parameters (operation 910). The process then selects settings for the device to cause the set of operational parameters to reach the values identified for the set of operational parameters (operation 912). The process then sends the settings to the device to control operation of the device (operation 914).

Figure 10:
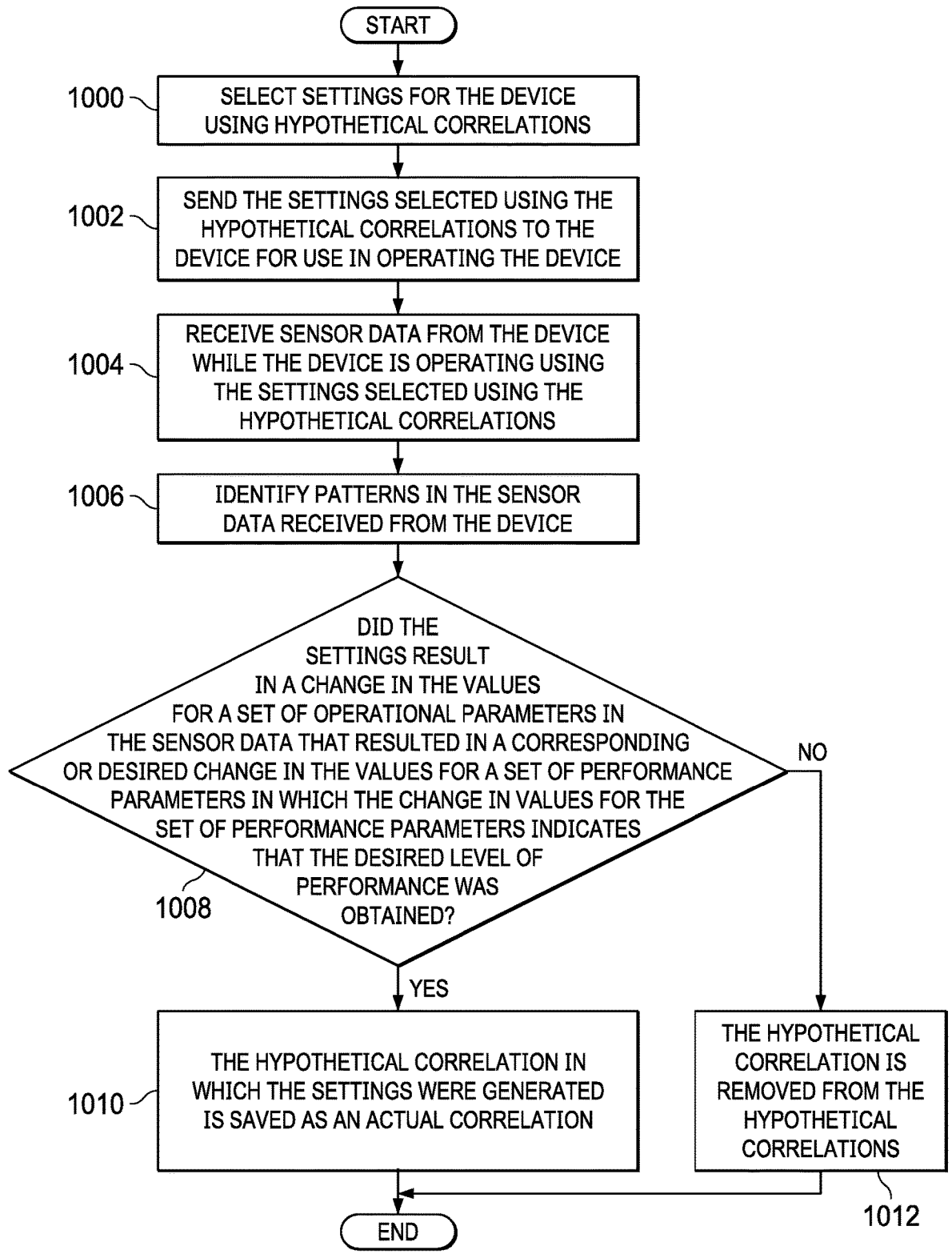
FIG. 10 is an illustration of flowchart of a process for determining actual correlations between patterns in aggregated sensor data in accordance with an illustrative example.

In FIG. 10, an illustration of flowchart of a process for determining actual correlations between patterns in aggregated sensor data is depicted in accordance with an illustrative example. The process in FIG. 10 can be implemented in hardware, software, or both. When implemented in software, the process can take the form of program code that is run by one or more processor units located in one or more hardware devices in one or more computer systems. For example, the process can be implemented in controller 208 in computer system 206 in FIG. 2 and in analyzer 240 in FIG. 4. As a more specific illustrative example, these processes can be implemented in artificial intelligence system 241 in FIG. 2 and artificial intelligence system 420 in FIG. 4.

The process begins by selecting settings for a device using hypothetical correlations (operation 1000). The selection of settings using the hypothetical correlations can be performed using the process illustrated in FIG. 10. In this illustrative example, settings can be based on values of operational parameters that can be measured for the device and values of the performance parameters that can be measured to determine the performance of the device.

The process sends the settings selected using the hypothetical correlations to the device for use in operating the device (operation 1002). The process receives sensor data from the device while the device is operating using the settings selected using the hypothetical correlations (operation 1004). The sensor data can be at least one of internal sensor data or external sensor data for the device.

The process identifies patterns in the sensor data received from the device (operation 1006). The process determines whether the settings resulted in a change in the values for a set of operational parameters in the sensor data that resulted in a corresponding or desired change in the values for a set of performance parameters in which the change in values for the set of performance parameters indicates that the desired level of performance was obtained (operation 1008). The determination can be made in operation 1008 by calculating correlation coefficients between the patterns identified in the sensor data. In the illustrative example, the patterns are between patterns that were determined to be hypothetically correlated between the patterns for operational parameters and the patterns for the performance parameters.

In this illustrative example, the data for the set of performance parameters may not be a single data point for a performance parameter but may be a range of data points that indicate that a desired level of performance has been reached.

If the settings resulted in the change in the values for the set of operational parameters in the sensor data that resulted in the corresponding or desired change in the values for set performance parameters values, the hypothetical correlation in which the settings were generated is saved as an actual correlation (operation 1010). The process terminates thereafter.

Otherwise, the hypothetical correlation is removed from the hypothetical correlations (operation 1012). The process terminates thereafter.

As a result, the feedback loop is present in which hypothetical correlations can be identified from patterns. Settings can be selected based on those patterns and sent to the device for use in operating the device. Sensor data received from the device using the settings are received and analyzed. The analysis can determine whether the settings resulted in the desired operation to confirm whether the hypothetical correlation is an actual correlation.

This process can be performed continuously to identify new correlations that may not have been previously identified as new sensor data is added to the aggregated sensor data. As a result, the illustrative examples using components such as an artificial intelligence system can identify correlations that may not have been previously known or possible to identify as new sensor data is received. In this manner, the artificial intelligence system can provide insights as to settings that can be used for the particular device to optimize the performance to reach the desired result. The identification of the correlations can be used in selecting the settings from other devices of the same class.

As a result, aggregated sensor data can be processed and transformed into patterns in correlations between the patterns. These correlations can be hypothetical correlations that can then be tested to determine whether they are actual correlations. The flowcharts and block diagrams in the different depicted examples illustrate the architecture, functionality, and operation of some possible implementations of apparatuses and methods in an illustrative example. In this regard, each block in the flowcharts or block diagrams can represent at least one of a module, a segment, a function, or a portion of an operation or step. For example, one or more of the blocks can be implemented as program code, hardware, or a combination of the program code and hardware. When implemented in hardware, the hardware can, for example, take the form of integrated circuits that are manufactured or configured to perform one or more operations in the flowcharts or block diagrams. When implemented as a combination of program code and hardware, the implementation may take the form of firmware. Each block in the flowcharts or the block diagrams can be implemented using special purpose hardware systems that perform the different operations or combinations of special purpose hardware and program code run by the special purpose hardware.

In some alternative implementations of an illustrative example, the function or functions noted in the blocks may occur out of the order noted in the figures. For example, in some cases, two blocks shown in succession may be performed substantially concurrently, or the blocks may sometimes be performed in the reverse order, depending upon the functionality involved. Also, other blocks may be added in addition to the illustrated blocks in a flowchart or block diagram.

Figure 11:
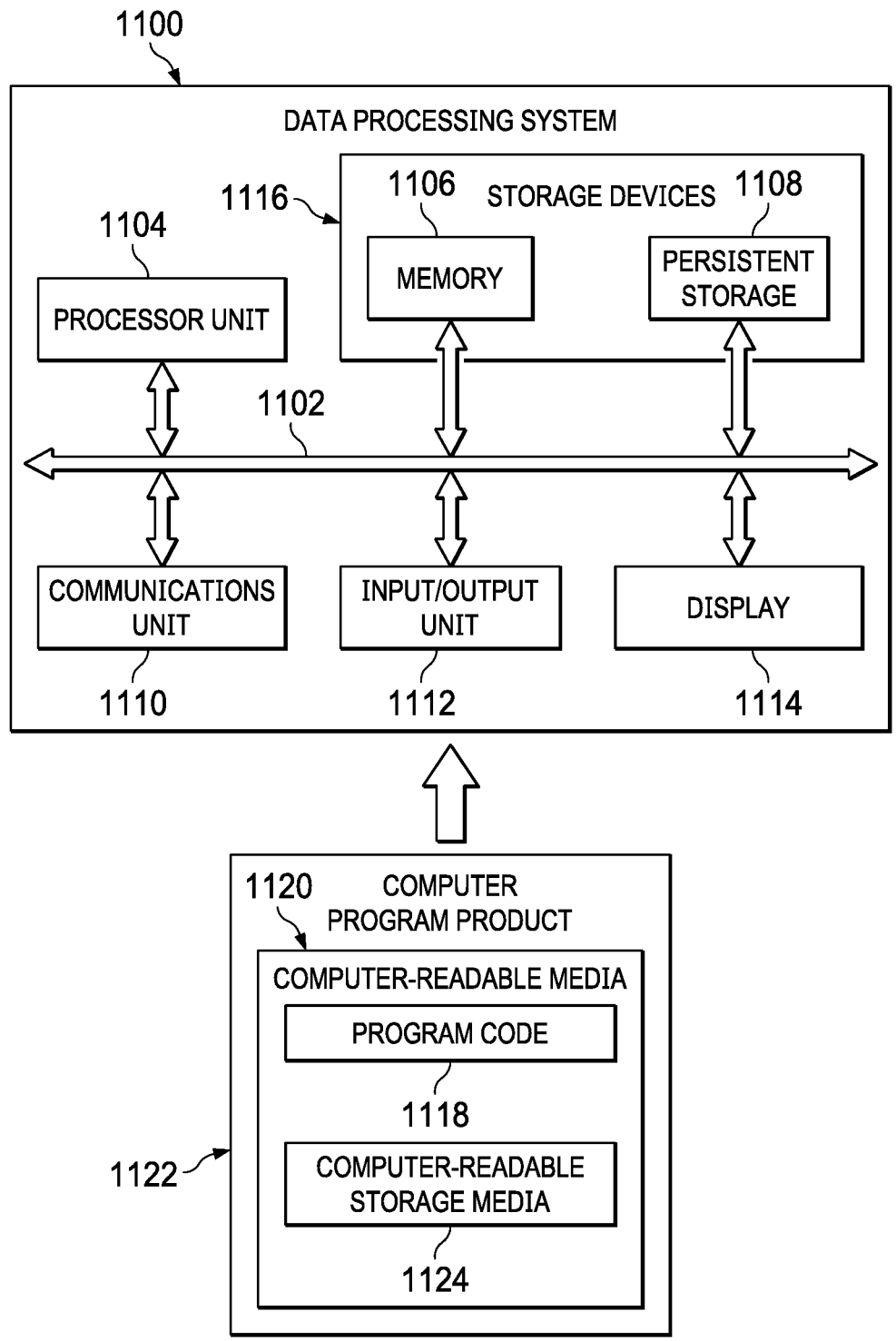
FIG. 11 is an illustration of a block diagram of a data processing system in accordance with an illustrative example.

Turning now to FIG. 11, an illustration of a block diagram of a data processing system is depicted in accordance with an illustrative example. Data processing system 1100 can be used to implement server computer 104, server computer 106, storage repository 108, and client devices 110 in FIG. 1. Data processing system 1100 can also be used to implement computer system 206 in FIG. 2, device 204 in FIG. 2, devices 232 in FIG. 2, and device 402 in FIG. 4. In this illustrative example, data processing system 1100 includes communications framework 1102, which provides communications between processor unit 1104, memory 1106, persistent storage 1108, communications unit 1110, input/output (I/O) unit 1112, and display 1114. In this example, communications framework 1102 takes the form of a bus system.

Processor unit 1104 serves to execute instructions for software that can be loaded into memory 1106. Processor unit 1104 includes one or more processors. For example, processor unit 1104 can be selected from at least one of a multicore processor, a central processing unit (CPU), a graphics processing unit (GPU), a physics processing unit (PPU), a digital signal processor (DSP), a network processor, or some other suitable type of processor.

Memory 1106 and persistent storage 1108 are examples of storage devices 1116. A storage device is any piece of hardware that is capable of storing information, such as, for example, without limitation, at least one of data, program code in functional form, or other suitable information either on a temporary basis, a permanent basis, or both on a temporary basis and a permanent basis. Storage devices 1116 may also be referred to as computer-readable storage devices in these illustrative examples. Memory 1106, in these examples, can be, for example, a random-access memory or any other suitable volatile or non-volatile storage device. Persistent storage 1108 can take various forms, depending on the particular implementation.

For example, persistent storage 1108 may contain one or more components or devices. For example, persistent storage 1108 can be a hard drive, a solid-state drive (SSD), a flash memory, a rewritable optical disk, a rewritable magnetic tape, or some combination of the above. The media used by persistent storage 1108 also can be removable. For example, a removable hard drive can be used for persistent storage 1108.

Communications unit 1110, in these illustrative examples, provides for communications with other data processing systems or devices. In these illustrative examples, communications unit 1110 is a network interface card.

Input/output (I/O) unit 1112 allows for input and output of data with other devices that can be connected to data processing system 1100. For example, input/output (I/O) unit 1112 can provide a connection for user input through at least one of a keyboard, a mouse, or some other suitable input device. Further, input/output (I/O) unit 1112 can send output to a printer. Display 1114 provides a mechanism to display information to a user.

Instructions for at least one of the operating system, applications, or programs can be located in storage devices 1116, which are in communication with processor unit 1104 through communications framework 1102. The processes of the different examples can be performed by processor unit 1104 using computer-implemented instructions, which can be located in a memory, such as memory 1106.

These instructions are referred to as program code, computer usable program code, or computer-readable program code that can be read and executed by a processor in processor unit 1104. The program code in the different examples can be embodied on different physical or computer-readable storage medium, such as memory 1106 or persistent storage 1108.

Program code 1118 is located in a functional form on computer-readable media 1120 that is selectively removable and can be loaded onto or transferred to data processing system 1100 for execution by processor unit 1104. Program code 1118 and computer-readable media 1120 form computer program product 1122 in these illustrative examples. In the illustrative example, computer-readable media 1120 is computer-readable storage medium 1124.

In these illustrative examples, computer-readable storage medium 1124 is a physical or tangible storage device used to store program code 1118 rather than a medium that propagates or transmits program code 1118. Computer readable storage medium 1124, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Alternatively, program code 1118 can be transferred to data processing system 1100 using a computer-readable signal media. The computer-readable signal media can be, for example, a propagated data signal containing program code 1118. For example, the computer-readable signal media can be at least one of an electromagnetic signal, an optical signal, or any other suitable type of signal. These signals can be transmitted over connections, such as wireless connections, optical fiber cable, coaxial cable, a wire, or any other suitable type of connection.

Further, as used herein, "computer-readable media 1120" can be singular or plural. For example, program code 1118 can be located in computer-readable media 1120 in the form of a single storage device or system. In another example, program code 1118 can be located in computer-readable media 1120 that is distributed in multiple data processing systems. In other words, some instructions in program code 1118 can be located in one data processing system while other instructions in in program code 1118 can be located in one data processing system. For example, a portion of program code 1118 can be located in computer-readable media 1120 in a server computer while another portion of program code 1118 can be located in computer-readable media 1120 located in a set of client computers.

The different components illustrated for data processing system 1100 are not meant to provide architectural limitations to the manner in which different examples can be implemented. In some illustrative examples, one or more of the components may be incorporated in or otherwise form a portion of, another component. For example, memory 1106, or portions thereof, can be incorporated in processor unit 1104 in some illustrative examples. The different illustrative examples can be implemented in a data processing system including components in addition to or in place of those illustrated for data processing system 1100. Other components shown in FIG. 11 can be varied from the illustrative examples shown. The different examples can be implemented using any hardware device or system capable of running program code 1118.

Thus, the illustrative examples provide a method, apparatus, system, and computer program product for controlling a device. One or more technical solutions are present that overcome a technical problem with making adjustments to a device to obtain desired operation of the device. As a result, one or more technical solutions can provide a technical effect of improving the performance of the device. One or more technical solutions can provide a technical effect in which a device can be controlled such that the operation of the device maintains a desired level of performance, reaches a desired level of performance, moves towards a desired level of performance, or some combination thereof.

A device control system comprises a computer system and a controller in the computer system. The controller receives internal sensor data for a group of internal parameters generated by an internal sensor system that senses the group of internal parameters within the device that relate to an operation of the device and receive external sensor data for a group of external parameters generated by an external sensor system that senses the group of external parameters in an environment around the device that relate to the operation of the device. The controller sends the internal sensor data and the external sensor data for an analysis with aggregated internal sensor data and aggregated external sensor data for devices of a same class as the device to generate results. The controller controls the operation of the device based on the results of the analysis.

One or more features of the illustrative examples are described in the following clauses. These clauses are examples of features not intended to limit other illustrative examples.

Clause 1.

A device control system comprising:

a computer system; and an artificial intelligence system in the computer system that is configured to:

receive internal sensor data for a group of internal parameters generated by an internal sensor system that senses the group of internal parameters within a group of devices in a same class;

receive external sensor data for a group of external parameters generated by an external sensor system that senses the group of external parameters in an environment around the group of devices in the same class;

aggregate the internal data for the group of internal parameters and the external data for the group of external parameters received from the devices of the same class as the device in a data storage system;

compare a performance level of a device to performance levels for the devices of the same class using the internal sensor data and the external sensor data with aggregated internal sensor data and aggregated external sensor data for the devices of the same class as the device to form a comparison;

determine whether a current status of the device is within a desired range based on the comparison; and send modifications to an operation of the device based on the comparison.

Clause 2.

The device control system of clause 1, wherein the data storage system comprises from at least one of a storage repository, a data lake, or a data warehouse.

The description of the different illustrative examples has been presented for purposes of illustration and description and is not intended to be exhaustive or limited to the examples in the form disclosed. The different illustrative examples describe components that perform actions or operations. In an illustrative example, a component can be configured to perform the action or operation described. For example, the component can have a configuration or design for a structure that provides the component an ability to perform the action or operation that is described in the illustrative examples as being performed by the component. Further, To the extent that terms "includes", "including", "has", "contains", and variants thereof are used herein, such terms are intended to be inclusive in a manner similar to the term "comprises" as an open transition word without precluding any additional or other elements.

Many modifications and variations will be apparent to those of ordinary skill in the art. Further, different illustrative examples may provide different features as compared to other desirable examples. The example or examples selected are chosen and described in order to best explain the principles of the examples, the practical application, and to enable others of ordinary skill in the art to understand the disclosure for various examples with various modifications as are suited to the particular use contemplated.

What is claimed is:

1. A device control system that comprises a computer system that comprises a controller configured to:

receive internal sensor data for a group of internal parameters generated by an internal sensor system that senses the group of internal parameters within a device that relate to an operation of the device, wherein the device is configured to communicate through a network with a server computer, and a storage repository that comprises aggregated internal sensor data and aggregated external sensor data;

receive external sensor data for a group of external parameters generated by an external sensor system that senses the group of external parameters in an environment around the device that relate to the operation of the device;

send the internal sensor data and the external sensor data to an artificial intelligence system in the server computer for an analysis with the aggregated internal sensor data and the aggregated external sensor data for devices within a same class as the device:

generate results; and control the operation of the device based on the results of the analysis.

2. The device control system of claim 1, further comprising an analyzer configured to:

analyze the internal sensor data and the external sensor data with the aggregated internal sensor data and the aggregated external sensor data for devices of the same class as the device; and generate the results based upon a machine learning model trained based upon analysis of the aggregated internal sensor data and the aggregated external sensor data for the devices of the same class as the device.

3. The device control system of claim 2, wherein the machine learning model is located in at least one of the device or a group of data processing systems in the computer system in a group of locations remote to the device.

4. The device control system of claim 1, further comprising an analyzer that is configured to:
compare a performance level of the device to performance levels for devices of the same class using the internal sensor data and the external sensor data with the aggregated internal sensor data and the aggregated external sensor data for the devices of the same class as the device to form a comparison in the results of the analysis; and
determine whether a current status of the device is within a desired level of performance based on the comparison.

5. The device control system of claim 4, wherein in controlling to the operation of the device, the controller is configured to:
adjust settings for the device.

6. The device control system of claim 4, wherein the results comprise a change in at least one of settings or program code for the device.

7. The device control system of claim 4, wherein in controlling the operation of the device based on the results of the analysis, the controller makes adjustments to the operation of the device using the results to obtain the desired level of performance for the device.

8. The device control system of claim 4, wherein the analyzer is located in at least of one of the device or a data processing system in the computer system in a location remote to the device.

9. The device control system of claim 8, further comprising:
a data storage system configured to stores the aggregated internal sensor data and the aggregated external sensor data for the devices of the same class as the device, wherein the data storage system comprises at least one of: a data lake, or a data warehouse.

10. The device control system of claim 9 further comprising:
an artificial intelligence system configured to aggregate internal data for the group of internal parameters and external data for the group of external parameters received from the devices of the same class as the device in the data storage system.

11. The device control system of claim 1 further comprising:
a human machine interface configured to send a set of commands to the controller, wherein the controller processes the set of commands to control the operation of the device.

12. The device control system of claim 1, wherein the internal sensor system comprises a group of internal Internet-of-things sensors.

13. The device control system of claim 1, wherein the external sensor system comprises a group of external Internet-of-things sensors.

14. The device control system of claim 1, wherein controlling the operation of the device based on the results of the analysis is automatically performed by the controller without requiring user input.

15. The device control system of claim 4, wherein the analyzer is located in at least one of the device, the controller, or a group of data processing systems in the computer system in a group of locations remote to the device.

16. The device control system of claim 1 further comprising:
a plurality of devices, wherein the device is part of the plurality of devices and the controller is configured to:
send the internal sensor data for the plurality of devices and the external sensor data for the plurality of devices for the analysis with the aggregated internal sensor data and the aggregated external sensor data for the devices of the same class as the plurality of devices generate the results; and
control the operation of the plurality of devices based on the results of the analysis.

17. The device control system of claim 1, wherein the device is selected from one of: a deep brain stimulation system, an infusion pump, a drug pump, a pacemaker, a defibrillator, an exoskeleton, a spacecraft, and a surface control system for an aircraft.

18. A device control system that comprises a computer system configured to:
receive internal sensor data for a group of internal parameters generated by an internal sensor system that senses the group of internal parameters within a device that relate to an operation of the device, wherein the device is configured to communicate through a network with a server computer, and a storage repository that comprises aggregated internal sensor data and aggregated external sensor data;
receive, in an artificial intelligence system in the server computer external sensor data for a group of external parameters generated by an external sensor system that senses the group of external parameters in an environment around the device that relate to the operation of the device;
generate results from an of the internal sensor data and the external sensor data with the aggregated internal sensor data and the aggregated external sensor data for devices within a same class as the device; and
control the operation of the device based on the results.

19. The device control system of claim 18, wherein in analyzing the internal sensor data and the external sensor data with the aggregated internal sensor data and the aggregated external sensor data for devices of the same class as the device to generate the results, the computer system is configured to:
analyze the internal sensor data and the external sensor data using a machine learning model trained using the aggregated internal sensor data and the aggregated external sensor data for the devices of the same class as the device to generate the results.

20. The device control system of claim 18, wherein in analyzing the internal sensor data and the external sensor data with the aggregated internal sensor data and the aggregated external sensor data for devices of the same class as the device to generate the results, the computer system is configured to:
compare a performance level of the device to performance levels for the devices of the same class using the internal sensor data and the external sensor data with the aggregated internal sensor data and the aggregated external sensor data for the devices of the same class as the device to form a comparison; and
determine whether a current status of the device is within a desired range based on the comparison.

21. The device control system of claim 20, wherein in controlling the operation of the device based on the results, the computer system adjusts the operation of the device to obtain a desired level of performance for the device.

22. The device control system of claim 20, wherein in controlling the operation of the device based on the results, the computer system is configured to:
adjust settings for the device.

23. The device control system of claim 19, wherein the machine learning model is located in a computer system in at least of one of the device or a group of data processing systems in the computer system in a group of locations remote to the device.

24. The device control system of claim 18, wherein the computer system is configured to:
send the internal sensor data and the external sensor data to a data storage system.

25. The device control system of claim 24, wherein the data storage system comprises at least one of a storage repository, a data lake, or a data warehouse.

26. The device control system of claim 25 further comprising:
an artificial intelligence aggregator configured to aggregate internal data for the group of internal parameters and external data for the group of external parameters received from devices of the same class as the device in the data storage system.

27. The device control system of claim 18 further comprising:
a human machine interface configured to send a set of commands to the computer system, wherein the computer system processes the set of commands to control the operation of the device.

28. The device control system of claim 18, wherein the internal sensor system comprises a group of internal Internet-of-things sensors.

29. The device control system of claim 18, wherein the external sensor system comprises a group of external Internet-of-things sensors.

30. The device control system of claim 18, wherein in controlling the operation of the device based on the results is automatically performed by the controller without requiring user input.

31. The device control system of claim 18, wherein the computer system comprises a controller configured to:
receive the internal sensor data for the group of internal parameters that relate to the operation of a set of devices in addition to the device, wherein the internal sensor data is generated by the internal sensor system;
receive the external sensor data for the group of external parameters for the environment around the set of devices, wherein the external sensor data is generated by an external sensor system;
analyze the internal sensor data and the external sensor data with aggregated internal sensor data and aggregated external sensor data for devices of the same class as the set of devices to generate results; and
control the operation of the set of devices based on the results.

32. The device control system of claim 31, wherein the device is selected from one of: a deep brain stimulation system, an infusion pump, a drug pump, a pacemaker, a defibrillator, an exoskeleton, or a surface control system for an aircraft.

33. A method for controlling a device, wherein the device is configured to communicate through a network with a server computer, and a storage repository that comprises aggregated internal sensor data and aggregated external sensor data, the method comprising:
receiving internal sensor data for a group of internal parameters that relate to an operation of the device, wherein the internal sensor data is generated by an internal sensor system;
receiving, in an artificial intelligence system in the server computer, external sensor data for a group of external parameters for an environment around the device, wherein the external sensor data is generated by an external sensor system;
generating results by analyzing the internal sensor data and the external sensor data with the aggregated internal sensor data and the aggregated external sensor data for devices within a same class as the device; and
controlling an operation of the device based on the results.

34. The method of claim 33, wherein in analyzing the internal sensor data and the external sensor data with the aggregated internal sensor data and the aggregated external sensor data for devices of the same class as the device to generate the results comprises:
analyzing the internal sensor data and the external sensor data using a machine learning model trained using the aggregated internal sensor data and the aggregated external sensor data for the devices of the same class as the device to generate the results.

35. The method of claim 34, wherein the machine learning model is located in at least of one of the device or a group of data processing systems in a computer system in a group of locations remote to the device.

36. The method of claim 34, wherein controlling the operation of the device based on the results comprises:
adjusting the operation of the device to obtain a desired level of performance for the device.

37. The method of claim 36, wherein adjusting to the operation of the device comprises:
adjusting settings for the device.

38. The method of claim 33 further comprising:
sending at least one of the internal sensor data, the external sensor data, or settings for the device to a data storage system.

39. The method of claim 38, wherein the data storage system comprises at least one of a storage repository, a data lake, or a data warehouse.

40. The method of claim 33, wherein the internal sensor system comprises a group of internal Internet of Things sensors.

41. The method of claim 33, wherein the external sensor system comprises a group of external Internet of Things sensors.

42. The method of claim 33, wherein controlling the operation of the device based on the results comprises:
controlling the operation of the device based on the results automatically without requiring user input.

43. The method of claim 33 further comprising:
receiving internal data for the group of internal parameters relating to the operation of a set of devices in addition to the device;
receiving external data for the group of external parameters for the environment around the set of devices;
analyzing the internal data and the external data with aggregated internal sensor data and aggregated external sensor data for devices of the same class as the set of devices to generate results; and
controlling the operation of the set of devices based on the results.

44. The method of claim 43, wherein the device and the set of devices are selected from at least one of: a deep brain stimulation system, an infusion pump, a drug pump, a pacemaker, a defibrillator, an exoskeleton, or a surface control system for an aircraft.

45. The device control system of claim 1 wherein another device is the same class as the device when the another device has characteristics that are sufficiently close to the device such that sensor data from the another device can be analyzed with a desired level of accuracy.

46. The device control system of claim 1 wherein devices of the same class are devices having same characteristics, and wherein at least one characteristic relates to a functionality of the device.

47. The device control system of claim 1 wherein devices of the same class are devices having same characteristics, and wherein at least one characteristic is a characteristic based on use of the device.

* * * * *

UNITED STATES PATENT AND TRADEMARK OFFICE
CERTIFICATE OF CORRECTION

| | |
|---|---|
| PATENT NO. | : 11,809,149 B2 |
| APPLICATION NO. | : 16/827462 |
| DATED | : November 7, 2023 |
| INVENTOR(S) | : Brian Dale Laughlin, Madi L. Laughlin and Dane B. Laughlin |

It is certified that error appears in the above-identified patent and that said Letters Patent is hereby corrected as shown below:

In the Claims

Column 38, Line 34, correct "generate results from an of the internal sensor data" to read --generate results from an analysis of the internal sensor data--

Signed and Sealed this
Twenty-first Day of May, 2024

Katherine Kelly Vidal
*Director of the United States Patent and Trademark Office*